(12) United States Patent
Yang

(10) Patent No.: US 8,178,307 B2
(45) Date of Patent: May 15, 2012

(54) METHODS AND COMPOSITIONS FOR DETECTION OF LETHAL CELL AND USES THEREOF

(75) Inventor: Shiaw-Der Yang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 54 days.

(21) Appl. No.: 12/553,035

(22) Filed: Sep. 2, 2009

(65) Prior Publication Data

US 2011/0053178 A1    Mar. 3, 2011

(51) Int. Cl.
  *G01N 33/53* (2006.01)
  *C12Q 1/68* (2006.01)
  *C07K 16/00* (2006.01)
(52) U.S. Cl. ............................ 435/7.1; 435/6; 530/387.1
(58) Field of Classification Search ........................ None
  See application file for complete search history.

(56) References Cited

U.S. PATENT DOCUMENTS 6,342,221 B1 * 1/2002 Thorpe et al. .............. 424/178.1

OTHER PUBLICATIONS

Chung, Chang, Yang, Lai, Hsu, Hsueh, Peng, Fu, Chang, and Yang. Association of proline-directed protein kinase FA with tumorigenesis, invasion and poor prognosis of human colon carcinoma. Cancer, 2002. vol. 95, pp. 1840-1847.*
Hsu, Fu, Jeng, Lee, and Yang. Proline directed protein kinase FA is a powerful and independent prognostic predictor for progression and patient survival of hepatocellular carcinoma. Journal of Clinical Oncology, 2006. vol. 24, pp. 3780-3788.*
AAD11986.1. Feb. 2, 1999.*
Campbell. Monoclonal Antibody Technology, 1984. pp. 1-32.*

* cited by examiner

*Primary Examiner* — Anne M. Gussow
(74) *Attorney, Agent, or Firm* — WPAT, P.C.; Anthony King

(57) ABSTRACT

The present invention relates to methods and compositions for identifying and detecting lethal cell useful for monitoring disease status and therapy response in various types of cancer patients regardless of the etiological origin of the cancer and uses thereof.

10 Claims, 11 Drawing Sheets

METHODS AND COMPOSITIONS FOR DETECTION OF LETHAL CELL AND USES THEREOF

BACKGROUND OF THE INVENTION

1. Field of the Invention

The present invention relates to methods and compositions for identifying and detecting lethal cell useful for monitoring disease status and therapy responses in various types of cancer patients regardless of the etiological origin of the cancer and uses thereof.

2. Prior Art

Although Hanahan and Weinberg in 2000 (Cell, 2000, 100:57-70) had enumerated the hallmarks of cancer, the currently-developed therapies based on this concept with major focus on the aggressive behavior of conventional cancer cells often failed to cure the cancer patients during the last 50 years. The recent studies have challenged that on some occasions, the incurable tumors, cancer cells and markers are merely the end products of the disease. There is increasing evidence that bone marrow-derived stem/progenitor cells (BMDSC) can be disseminated throughout the body and continually recruited in a variety of situations to the stroma of developing tumors closely resembling overhealing wounds which entail the constant deposition of growth factors, chemokines, cytokines and tissue-remodeling factors that can gradually destroy the organ microenvironments resulting in organ failures and simultaneously pave the milestones to facilitate host-immunosuppression, anti-apoptosis, malignant transformation of epithelia, proliferation, growth, invasion, and metastatic spread of cancer cells. However, the controversial and paradoxical roles of BMDSC comprising various types of stem/progenitor cells and derivatives such as fibroblasts and macrophages in incurable cancer development and progression remain a great challenge to solve the current cancer problems (Bingle et al, *J Pathol*, 2002, 196:254-265; De Wever and Mareel, *J Pathol*, 2003, 200:429-447; Condeelis and Pollard, *Cell*, 2006, 124:263-266; Direkze and Alison, *Hematol Oncol*, 2006, 24:189-195; Kaplan et al, *Trends Mol Med*, 2007, 13:72-81; Karnoub et al, *Nature*, 2007, 449:557-563; Loberg et al, *CA Cancer J Clin*, 2007, 57:225-241; Massberg et al, *Cell*, 2007, 131:994-1008; Biswas et al, *J Immunol*, 2008, 180:2011-2017; Chantrain et al, *Cancer Microenviron*, 2008, 1:23-35; Germano et al, *Cytokine*, 2008, 43:374-379; Laird et al, *Cell*, 2008, 132:612-630; Le Bitoux and Stamenkovic, *Histochem Cell Biol*, 2008, 130:1079-1090; Takaishi et al, *J Clin Oncol*, 2008, 26:2876-2882; Aggarwal and Gehlot, *Curr Opin Pharmacol*, 2009, 9:1-19; Gonda et al, *Cell Cycle*, 2009, 8:2005-2013; Joyce and Pollard, *Nat Rev Cancer*, 2009, 9:239-252; Mishra et al, *Cancer Res*, 2009, 69:1255-1258; Psaila and Lyden, *Nat Rev Cancer*, 2009, 9:285-293). It has been challenged that besides the traditional molecular oncology study with major focus on conventional cancer cells during the last 50 years, the cellular and clinical oncology studies and more particularly the systemic oncology study should be simultaneously emphasized.

Proline-directed protein kinase $F_A$ (PDPK $F_A$)/glycogen synthase kinase-3α (GSK-3α) was originally identified as a specific protein phosphatase activating factor A (Vandenheede et al, *J Biol Chem*, 1980, 255:11768-11774; Yang et al, *J Biol Chem*, 1980, 255:11759-11767; Woodgett, *EMBO J*, 1990, 9:2431-2438). In this lab, PDPK $F_A$/GSK-3α was further characterized as a multisubstrate/multifunctional PDPK associated with anti-apoptosis, anti-differentiation, tumorigenesis, invasion and chemoresistance of various types of conventional cancer cells (Lee et al, *J Cell Biochem*, 1995, 58:474-480; Yang et al, *J Cell Biochem*, 1995, 59:143-150; Yang et al, *J Cell Biochem*, 1996, 61:238-245; Hsu et al, *Br J Cancer*, 2000, 82:1480-1484; Hsu et al, *Cancer*, 2000, 89:1004-1011; Yang et al, *Clin Cancer Res*, 2000, 6:1024-1030; Hsu et al, *Cancer*, 2001, 92:1753-1758; Hsu et al, *Int J Cancer*, 2001, 91:650-653; Chung et al, *Cancer*, 2002, 95:1840-1847; Hsueh et al, *Cancer*, 2002, 95:775-783; Fu and Yang, *Anticancer Res*, 2004, 24:1489-1494; Yang, *Curr Cancer Drug Targets*, 2004, 4:591-596; Yang, *Drug News Perspect*, 2005, 18:432-436; Hsu et al, *J Clin Oncol*, 2006, 24:3780-3788). Unfortunately, the previous work on PDPK $F_A$/GSK-3α was mainly associated with the current mainstream cancer research with major focus on conventional cancer or precancer cells as described above. The impact of this signal transducing molecule in cancer therefore remains to be evaluated.

SUMMARY OF THE INVENTION

In contrast to the previous work on PDPK $F_A$/GSK-3α which was mainly associated with the mainstream cancer research with major focus on conventional cancer cells as described above, the present invention was to examine the role of this signal transducing PDPK particularly in bone marrow-derived stem/progenitor cells (BMDSC) which can be recruited and homing to the stromas of developing tumors closely resembling the overhealing wounds as described above. By using such novel approaches, the aberrant expressions of PDPK $F_A$/GSK-3α in BMDSC were demonstrated to play a determinant and instructional role in monitoring the disease status and therapy response and in determining if the diseases are curable or incurable in various types of tumors associated with a variety of vital organs. Cancer patients if associated with aberrant expressions of PDPK $F_A$/GSK-3α in BMDSC tend to be beyond curable regardless of the etiological origin of the diseases. Thus, the BMDSC if associated with aberrant expressions of PDPK $F_A$/GSK-3α was collectively termed "lethal cell" in this invention. In contrast to the previous work on conventional cancer cells, the present invention provides methods and compositions for detection of lethal cell, a newly-described aggressive cell for universal application to cancer prevention, treatment and uses thereof. For instance, the early-stage cancer patients if not associated with a lethal cell tend to be curable by local excisions. In contrast, the early-stage cancer patients if associated with a lethal cell tend to be incurable by surgery. Thus, this invention provides methods and compositions for monitoring therapy response to help medical doctors make decision for more aggressive and appropriate treatments. The lethal cell provided herein represents a universally applicable predictor useful for very early detection of systemic deregulation and imbalance of hematopoiesis, hemastasis, homeostasis, and immune system in association with systemic immune suppression, infections, obstructions, emboli and multiple organ failures originated from intrinsic defect in bone marrow. More particularly, the lethal cell is a reliable predictor for monitoring the disease status and therapy responses in various types of cancer patients. On the other hand, PDPK $F_A$/GSK-3α may not necessarily represent the most powerful and ideal candidate to target for drug screening. However, by using this signal transducing molecule as a novel probe, this invention provides methods and compositions for detection and isolation of lethal cell that plays a determinant role in monitoring therapy responses and cancer progression. Thus, the lethal cell presented in this invention, when isolated, provide methods and compositions for the development of proteomics and genomics global expression profiles for therapeutic drugs screening and evaluations for more efficacious and comprehensive preventions and treatments of various types of human cancers regardless of the etiological origin of the cancer and uses thereof.

Thus, in one aspect, provided herein is a method for detecting the presence of a cellular expression profile in a bone marrow-derived stem/progenitor cell (BMDSC) in a subject indicative of a lethal cell, which method comprises obtaining a biological sample from said subject; determining the expression of PDPK $F_A$/GSK-3α in BMDSC in said sample wherein an aberrant intracellular accumulation of PDPK $F_A$/GSK-3α in BMDSC of said subject indicates the presence of a lethal cell. In some embodiments, the expression of PDPK $F_A$/GSK-3α is determined by assaying PDPK $F_A$/GSK-3α protein levels such as an immunoassay using antibodies specific for PDPK $F_A$/GSK-3α. The biological sample can be bone marrow, blood, tissue, tumor, ascites or pleural effusions.

In another aspect, provided herein is a diagnostic kit for determining the presence of a lethal cell in a biological sample comprising at least one reagent for determining the expression of PDPK $F_A$/GSK-3α in said sample, and printed instructions for assessing the presence of a lethal cell, packaged together in a container. Further detection reagents may also be included.

Furthermore, in another aspect, provided herein is a method for monitoring therapy response and disease progression in various types of cancer patients regardless of the etiological origin of the cancer, which method comprises obtaining a biological sample from said subject; determining the expression of PDPK $F_A$/GSK-3α in said sample wherein an aberrant intracellular accumulation of PDPK $F_A$/GSK-3α in said subject. In some embodiments, the expression of PDPK $F_A$/GSK-3α is determined by assaying PDPK $F_A$/GSK-3α protein levels such as an immunoassay using antibodies specific for PDPK $F_A$/GSK-3α. The biological sample can be bone marrow, blood, tissue, tumor, ascites or pleural effusions.

If necessary, the cell can be isolated for detection of lethal cell highly expressing PDPK $F_A$/GSK-3α by specific magnetic beads or flow cell sorter essentially as described by Moioli et al (PLoS ONE, 3:e3922, 2008).

These and other objects and features of the invention will become more fully apparent when the following detailed description is read in conjunction with the accompanying figures and examples.

DETAILED DESCRIPTION OF THE INVENTION

Figure 1:
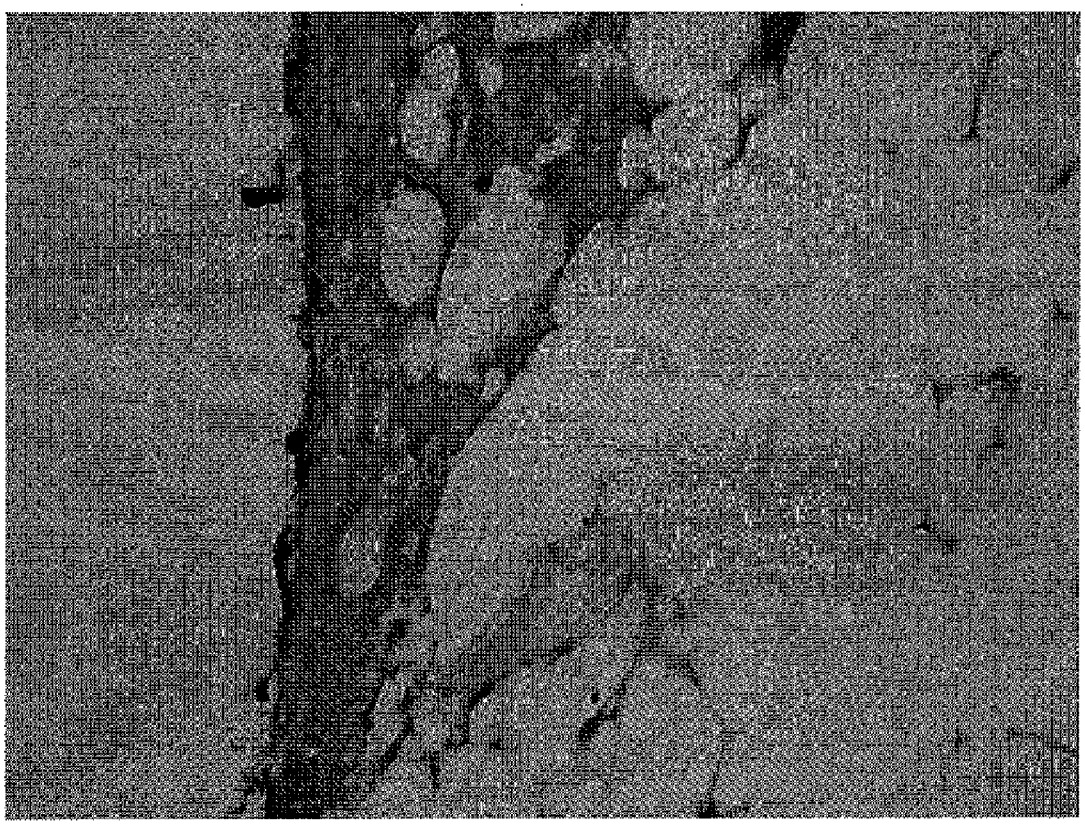
FIG. 1 depicts the acute myelogenous leukemia (AML) patients if associated with a lethal cell in their bone marrow tend to have pneumonia progression and/or failures in bone marrow transplantations (A, B). Conversely, the AML patients if not associated with a lethal cell tend to have favorable outcome after treatment or bone marrow transplantations (C).
Figure 1:
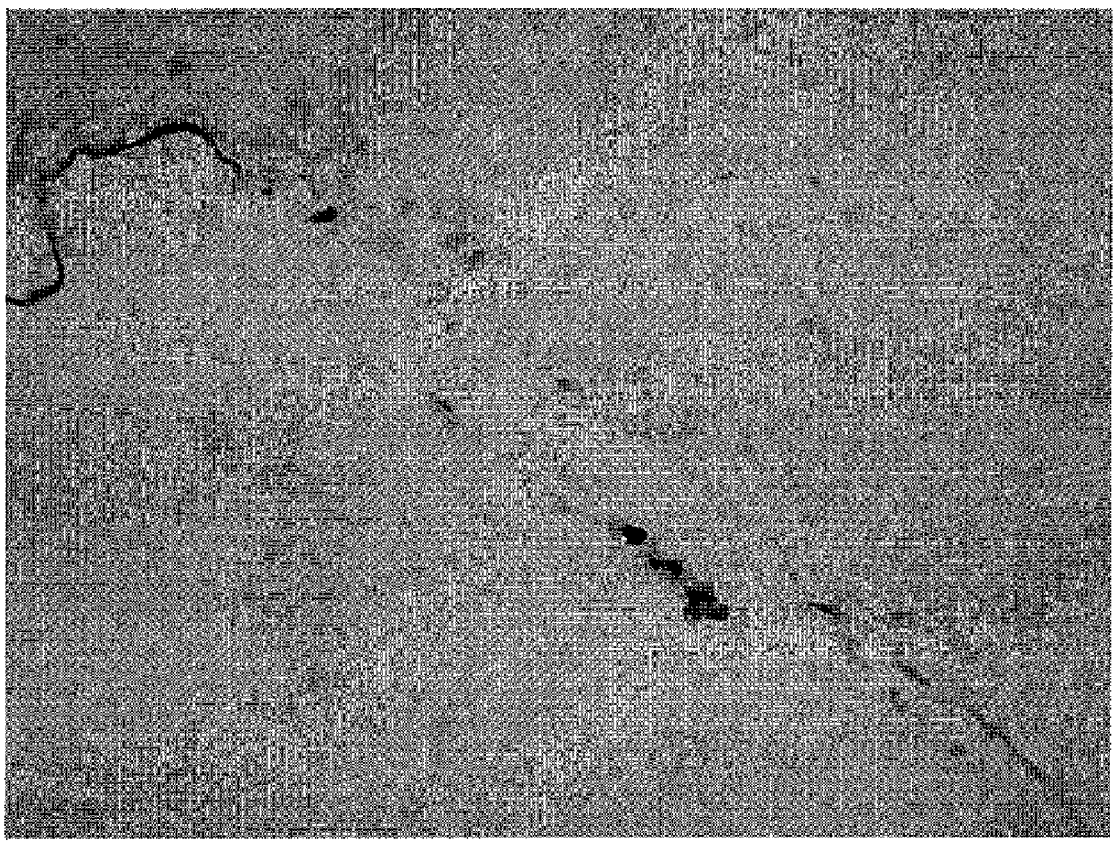
Figure 1:
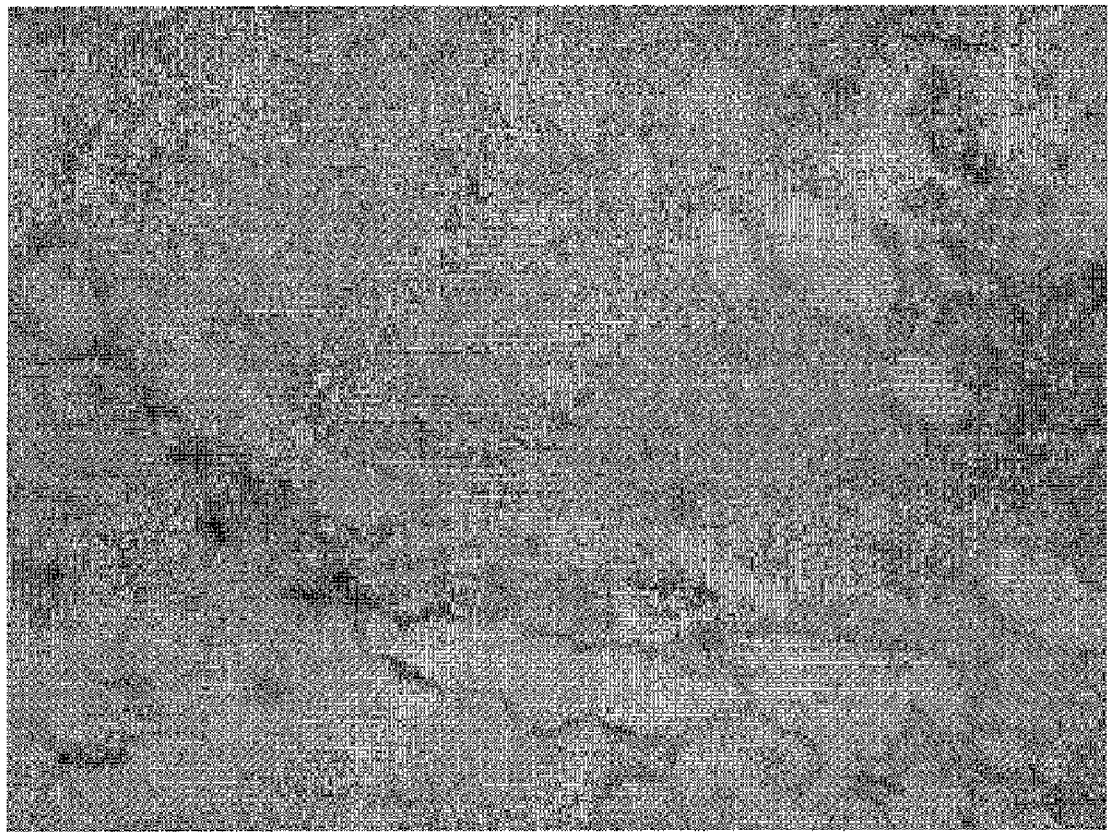

For clarity of disclosure, and not by way of limitation, the detailed description of the invention is divided into the subsections that follow.

A. DEFINITION

Unless defined otherwise, all technical and scientific terms used herein have the same meaning as is commonly understood by one of ordinary skill in the art to which this invention belongs. All patents, applications, published applications and other publications, and Genbank Accession numbers referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "PDPK $F_A$/GSK-3α" refers to the multisubstrate/multifunctional proline-directed protein kinase $F_A$ also known as glycogen synthase kinase-3alpha (Woodgett, *EMBO J,* 1990, 9:2431-2438; Yang, *Curr Cancer Drug Targets,* 2004, 4:591-596). The Genbank Accession numbers for this protein are AAD11986 and AAH27984.

As used herein, "biological sample" refers to any sample from a biologic source, including bone marrow, blood, tissue, tumor, ascites or pleural effusions.

As used herein, the term "antibody" refers to an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and Fab2, so long as they exhibit the desired biological activity, e.g., specifically bind PDPK $F_A$/GSK-3α.

As used herein, the term "lethal cell" refers to a BMDSC associated with an aberrant intracellular accumulation of PDPK $F_A$/GSK-3α.

Unless otherwise indicated, all terms used herein have the same meaning as they would to one skilled in the art and the practice of this invention will be employed, conventional techniques of biochemical and clinical pathological technology, which are within the knowledge of those of skill of the art.

B. METHODS AND KITS FOR DETECTING LETHAL CELL

In one aspect, a BMDSC associated with an aberrant intracellular accumulation of PDPK $F_A$/GSK-3α offers a tool to identify and detect lethal cell. In another aspect, identification of lethal cell in a biological sample is useful for monitoring the therapy response and disease status of various types of cancer patients regardless of the etiological origin of the cancer.

Thus, in one aspect, provided herein is a method for detecting the presence of a cellular expression profile in a subject indicative of a lethal cell, which method comprises obtaining a biological sample from said subject; determining the expression of PDPK $F_A$/GSK-3α in BMDSC in said sample wherein an aberrant intracellular accumulation of PDPK $F_A$/GSK-3α in BMDSC of said subject indicates the presence of a lethal cell. In some embodiments, the expression of PDPK $F_A$/GSK-3α is determined by assaying PDPK $F_A$/GSK-3α protein level such as an immunoassay using antibodies specific for PDPK $F_A$/GSK-3α. The biological sample can be bone marrow, blood, tissue, tumor, ascites or pleural effusions.

In another aspect, provided herein is a kit for determining the presence of a lethal cell in a biological sample comprising at least one reagent for determining the expression of PDPK $F_A$/GSK-3α in a BMDSC in said sample, and printed instructions packaged together in a container.

Any suitable means of detecting aberrant expressions of PDPK $F_A$/GSK-3α in BMDSC may be employed. The expression can be determined by assessing protein levels in BMDSC from a biological sample. For example, an immunoassay using an antibody specific for PDPK $F_A$/GSK-3α may be employed. Suitable means include, but are not limited to immunohistochemical analysis, immunocytochemical analysis and flow cytometry analysis. With immunohistochemical staining techniques, a cell sample is prepared, typically by dehydration and fixation, followed by reaction with labeled antibodies specific for the gene product coupled, where the labels are usually visually detectable, such as enzymatic labels, florescent labels, luminescent labels, and the like.

According to one embodiment, tissue samples are obtained from subjects and the samples are embedded then cut to e.g. 3-5 μm, fixed, mounted and dried according to conventional tissue mounting techniques. The fixing agent may comprise formalin. The embedding agent for mounting the specimen may comprise, e.g., paraffin. The samples may be stored in this condition. Following deparaffinization and rehydration, the samples are contacted with an immunoreagent comprising an antibody specific for PDPK $F_A$/GSK-3α. The antibody may comprise a polyclonal or monoclonal antibody. The antibody may comprise an intact antibody, or fragments thereof capable of specifically binding PDPK $F_A$/GSK-3α protein. Appropriate polyclonal antisera or other antibody may be prepared by immunizing appropriate host animals with PDPK $F_A$/GSK-3α protein, or a suitable fragment thereof, and collecting and purifying the antisera according to conventional techniques known to those skilled in the art. Monoclonal or polyclonal antibodies specifically reacting with PDPK $F_A$/GSK-3α, may be made by methods well known in the art. See, e.g., Harlow and Lane (1988) Antibodies: A Laboratory Manual, Cold Spring Harbor Laboratories; Goding (1986) Monoclonal Antibodies: Principles and Practice, 2d ed., Academic Press, New York. Also, recombinant antibodies may be produced by methods known in the art, including but not limited to, the methods described in U.S. Pat. No. 4,816,567, or obtained commercially.

The antibody either directly or indirectly bears a suitable detectable label. Alternatively, the detectable label can be attached to a secondary antibody, e.g., goat anti-rabbit IgG, which binds the primary antibody. Frequently, the polypeptides and antibodies are labeled by joining, either covalently or noncovalently, a substance which provides a detectable signal. Suitable labels include, but are not limited to, radionuclides, enzymes, substrates, cofactors, inhibitors, fluorescent agents, chemiluminescent agents, magnetic particles and the like.

Any suitable means can be used to obtain a biological sample from a subject. A biological sample can be bone marrow, blood, tissue, tumor, ascites or pleural effusions.

Kits for monitoring therapy response and disease status in various types of cancer patients regardless of the etiological origin of the cancer will include at least one container sized to house at least one reagent useful in determining the expression of PDPK $F_A$/GSK-3α in BMDSC as defined herein, and printed instructions for assessing whether or not BMDSC in a biological sample contain a lethal cell. As used herein, the term "reagent" means any compound, composition or biological agent (i.e., samples, aliquots or "doses" of cells, antibodies, etc.) useful in carrying out any method provided herein, including but not limited to antibodies for PDPK $F_A$/GSK-3α, buffers and carriers for analysis.

C. EMBODIMENTS

Unless otherwise indicated in the specific embodiments, all immunohistochemical analysis, immunophenotyping analysis, immunocytochemical analysis and statistical analysis followed the below methods.

Production, Identification and Characterization of Specific Anti-PDPK $F_A$/GSK-3α Antibody. The peptide QST-DATPTLTNSS, corresponding to the carboxyl terminal region from amino acids 471 to 483 of the sequence of PDPK $F_A$/GSK-3α was synthesized by peptide synthesizer (model 9050, Milligen, Bedford, Mass.). The cysteine residue was added to the NH2 terminus in order to facilitate coupling of the peptide to bovine serum albumin according to the procedure described by Reichlin (1980) using glutaraldehyde as the cross-linker. The antibody production has been through affinity purification and the recognition that could be blocked by the C-terminal peptide from amino acids 471-483 of PDPK $F_A$/GSK-3α to demonstrate the immunospecificity of this anti-PDPK $F_A$/GSK-3α antibody.

Immunohistochemical Analysis. Tissue sections (5 μm) of formalin-fixed, paraffin-embedded tissue containing tumor that showed the maximum extent of tumor cells were dewaxed in xylene and rehydrated in graded concentrations of ethanol. Endogenous peroxidase was blocked with 3% hydrogen peroxide followed by bovine serum albumin blocking for 5 minutes. The slides were next incubated with anti-PDPK $F_A$/GSK-3α antibody (2 μg/mL) diluted in 0.05 M Tris buffer, pH 7.4, at 4° C. for 16 hours followed by 20-minute incubation at room temperature with super enhancer (Super Sensitive™ Non-Biotin Detection System, [BioGenex, San Ramon, Calif.]), and another 30-minute incubation with polymer-HRP (Super Sensitive™) label. Immunostaining was finally developed with DAB (3-3' diaminobenzidine tetrahydrochloride), resulting in a red-to-brown color. After quenching the enzyme reaction, slides were incubated in DS-enhancer (Zymed, San Francisco, Calif.) at room temperature for five minutes to prevent the interaction between two staining system. Then, slides were incubated with CD34 antibody for one hour at room temperature. After washing, slides were incubated with anti-mouse alkaline phosphatase for 30 minutes at room temperature. BCIP/NBT solution was used for visualization of the bound antibody, resulting in a blue color. Sections were counterstained with methyl green solution, resulting in a green color. Cells co-staining with PDPK $F_A$/GSK-3α and CD34 have a purple-to-black color.

Immunocytochemical Analysis. Cells will be cytocentrifuged onto polylysine-coated slides at 700 rpm for 3 minutes at room temperature (Kubota 5200, Japan). Before staining, the cytospots will be fixed with 3.7% paraformaldehyde for 15 minutes and treated with 0.2% triton X-100 for 90 seconds.

Endogenous peroxidase will be blocked with 3% hydrogen peroxide followed by bovine serum albumin blocking for 10 minutes. The slides will be incubated with anti-PDPK $F_A$/GSK-3α antibody (2 μg/mL) diluted in 0.05 M Tris buffer, pH 7.4, at 4° C. for 16 hours followed by 20-minute incubation at room temperature with super enhancer (Super Sensitive™ Non-Biotin Detection System, [BioGenex, San Ramon, Calif.]), and another 30-minute incubation with polymer-HRP (Super Sensitive™) label. Immunostaining was finally developed with DAB (3-3' diaminobenzidine tetrahydrochloride), resulting in a red-to-brown color. After quenching the enzyme reaction, slides were incubated in DS-enhancer (Zymed, San Francisco, Calif.) at room temperature for five minutes to prevent the interaction between two staining system. Then, slides were incubated with CD34 antibody for one hour at room temperature. After washing, slides were incubated with anti-mouse alkaline phosphatase for 30 minutes at room temperature. BCIP/NBT solution was used for visualization of the bound antibody, resulting in a blue color. Sections were counterstained with methyl green solution, resulting in a green color. Cells co-staining with PDPK $F_A$/GSK-3α and CD34 have a purple-to-black color.

Statistical Analysis. In the statistical analyses, the samples were dichotomized as with versus without the presence of a lethal cell. Overall survival was calculated from the date of diagnosis to the date of death or last follow-up. Disease-free survival was measured from the date of diagnosis to the date of recurrence, metastasis, death or last follow-up. The Kaplan-Meier method was used to determine the survival probability, and the log-rank test was used to compare the survival curves between groups. The impact of was analyzed by the Cox proportional hazards regression model. Logistic regression was used to calculate the risk of the presence of a lethal cell in therapy response. P<0.05 was considered statistically significant.

The study was performed under the approved research projects and grants from National Science Council in Taiwan and approved by the informed consents and the Institution's Surveillance and Ethics Committee.

The following examples are offered to illustrate but not to limit the invention.

Example I

Association of Aberrant Expressions of PDPK $F_A$/GSK-3α in BMDSC with Poor Prognosis of Acute Myelogeneous Leukemia (AML) Patients Even after Aggressive Treatments Aberrant expressions of PDPK $F_A$/GSK-3α could be frequently detected in bone marrow of AML patients with disease progression. Immunophenotyping analysis revealed that a rare population of CD34+ hematopoietic stem/progenitor cells and CD34− mesenchymal stem/progenitor cells collectively termed BMDSC (Moioli et al, *PLoS ONE,* 2008, 3:e3922) associated with an aberrant intracellular accumulation of PDPK $F_A$/GSK-3α (FIGS. 1A and B) could be frequently detected in bone marrow of AML patients with poor prognosis; more than 75% of such type of patients died even after aggressive treatments. In sharp contrast, more than 80% of AML patients without the presence of such type of BMDSC in bone marrow (FIG. 1C) were cured after the treatments. Thus, the BMDSC if associated with an aberrant intracellular accumulation of PDPK $F_A$/GSK-3α was collectively termed "lethal cell" throughout the text of this invention. The initial independent cohort study revealed that AML patients if associated with a lethal cell as shown in FIGS. 1A and B tend to have poor outcome after treatments. In sharp contrast, AML patients if not associated with a lethal cell as shown in FIG. 1C tend to have favorable outcome after treatments. Thus, this invention provides methods and compositions for the detection of lethal cell and uses thereof.

Example II

Lung Cancer Patients if Associated with a Lethal Cell Tend to have Very Unfavorable Outcome and Poor Therapy Response Lung cancer is the most common cause of cancer-related death worldwide. Despite recent therapeutic advances, the prognosis of patients with lung cancer is still unsatisfactory. The majority of patients develops recurrent disease and eventually dies of metastasis disease even after complete tumor resection. To date, the tumor-node-metastasis staging system of lung cancer is widely used as a guide for predicting prognosis. However, prognosis of patients with the same stage lung cancer, particularly in the early-stage of the disease, are heterogeneous and a strategy to establish appropriate therapeutic modalities for each patient has not been formulated. Therefore, more reliable biomarkers implicated in the biologic function that affect tumor progression and metastasis should be sought to identify subgroups among patients within the same stage who are most at risk for poor outcome.

There were 156 lung cancer patients who had complete clinicopathologic data and specimen available for lethal cell study. The clinicopathologic features of the patients studied were summarized in Table 1. Of 156 patients studied (100 male and 56 female) with ages ranging from 23 to 82 years (mean, 62 years), the average tumor size was 3.9±2.3 cm (mean±SD; median, 3 cm). Seventy-two patients (46.2%) had a history of smoking. With regard to histological type, 117 patients (75.0%) were adenocarcinoma, 36 patients (23.1%) were squamous cell carcinoma and 3 patients (1.9%) were large cell carcinoma. The extents of differentiation were graded as well-differentiated in 42 patients (26.9%), moderately-differentiated in 65 patients (41.7%) and poorly-differentiated in 49 patients (31.4%). The pathologic t status was classified as T1 in 50 patients (32.1%), T2 in 59 patients (37.8%), T3 in 30 patients (19.2%) and T4 in 17 patients (10.9%). There were 29 patients (18.6%) in N1 level lymph node involvement, 21 patients (13.5%) in N2 level and 12 patients (7.7%) in N3 level, whereas 94 patients (60.3%) were not in lymph node involvement. The lung cancer patients were classified as stage I, II, III, and IV in 69 patients (44.2%), 23 patients (14.7%), 55 patients (35.3%) and 9 patients (5.8%), respectively. Five-year disease-free survival and overall survival of the 156 lung cancer patients were 36.6% and 45.3%, respectively.

TABLE 1

The Lung Cancer Patients Characteristics

| | | Case number | Percentage (%) |
|---|---|---|---|
| Age (years)[†], Mean ± SD | | 62.0 ± 11.1 | |
| Gender | Male | 100 | 64.1 |
| | Female | 56 | 35.9 |
| Smoking history | Nonsmoker | 84 | 53.8 |
| | Smoker | 72 | 46.2 |

TABLE 1-continued

The Lung Cancer Patients Characteristics

|  |  | Case number | Percentage (%) |
|---|---|---|---|
| Tumor size (cm)[†], Mean ± SD |  | 3.9 ± 2.3 | |
| CEA (ng/mL)[†], Mean ± SD |  | 7.0 ± 14.3 | |
| Histology | Adenocarcinoma | 117 | 75.0 |
|  | Squamous cell carcinoma | 36 | 23.1 |
|  | Large cell carcinoma | 3 | 1.9 |
| Differentiation | Well | 42 | 26.9 |
|  | Moderate | 65 | 41.7 |
|  | Poor | 49 | 31.4 |
| Depth of tumor invasion | T1 | 50 | 32.1 |
|  | T2 | 59 | 37.8 |
|  | T3 | 30 | 19.2 |
|  | T4 | 17 | 10.9 |
| Lymph node metastasis | N0 | 94 | 60.3 |
|  | N1 | 29 | 18.6 |
|  | N2 | 21 | 13.5 |
|  | N3 | 12 | 7.7 |
| Stage | I | 69 | 44.2 |
|  | II | 23 | 14.7 |
|  | III | 55 | 35.3 |
|  | IV | 9 | 5.8 |
| Recurrence | Negative | 54 | 34.0 |
|  | Positive | 103 | 66.0 |
| Metastasis | Negative | 106 | 67.9 |
|  | Positive | 50 | 32.1 |
| Lethal cell | Negative | 76 | 48.7 |
|  | Positive | 80 | 51.3 |

Abbreviations:
CEA, carcinoembryonic antigen;
pT, pathological T status;
pN, pathological N status
[†]The results of continuous variable are expressed as mean ± SD.

Figure 2:
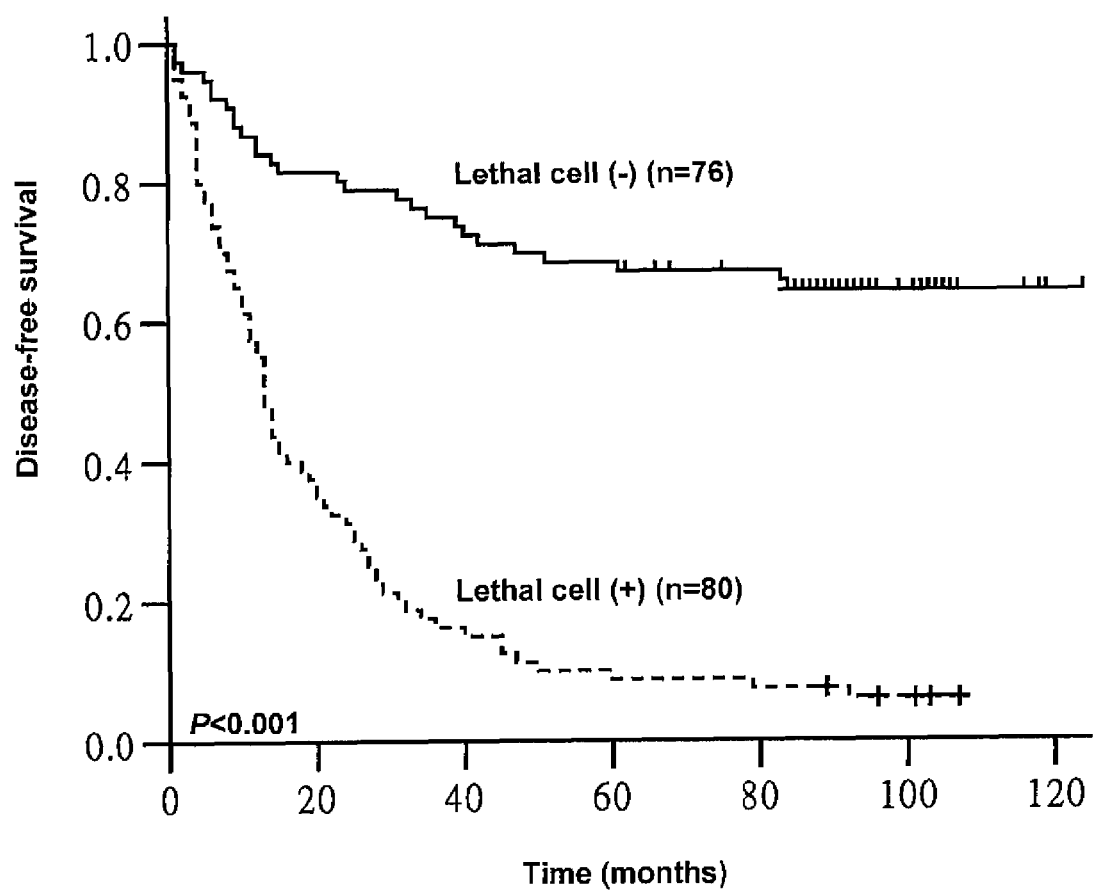
FIG. 2 depicts the disease-free survival (A) and overall survival (B) of lung cancer patients with respect to lethal cell.
Figure 2B:
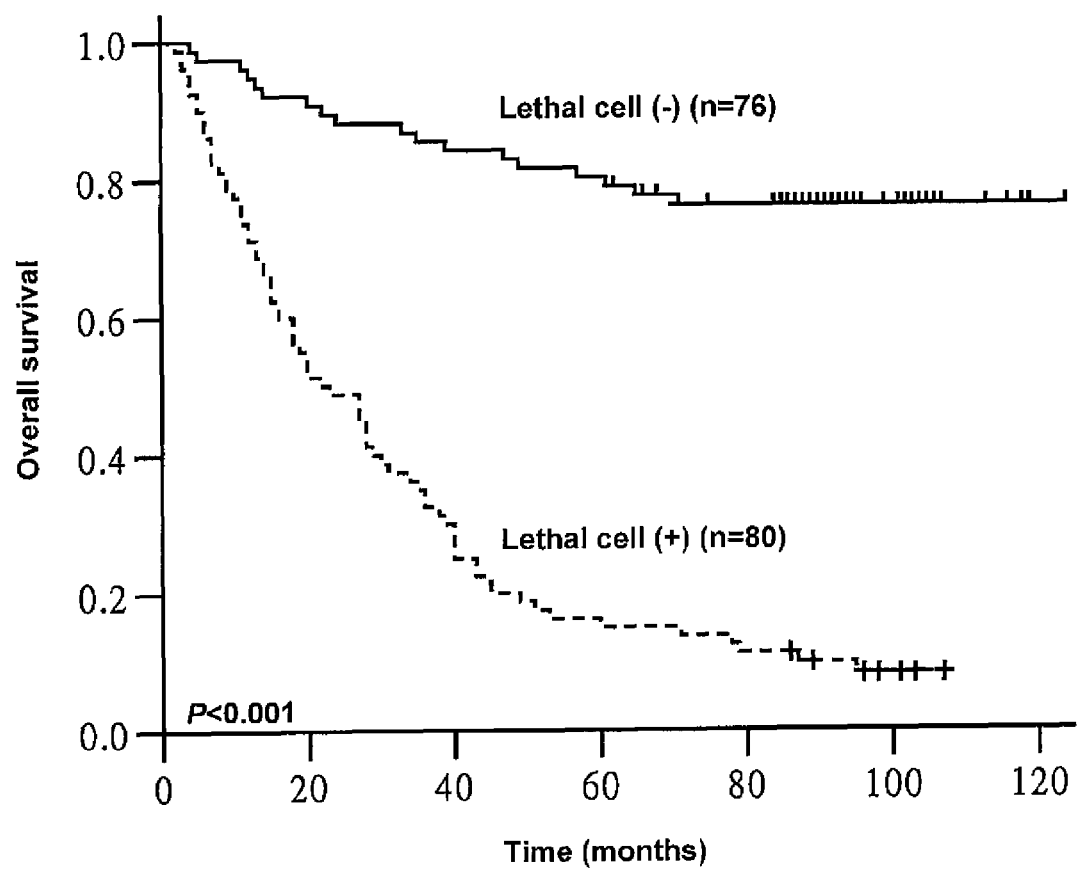

The patients characteristics in this study were similar to the current epidemiologic status, indicating that the results obtained from these cases in an independent cohort study are applicable to lung cancer worldwide. It was therefore decided to use this representative study population to evaluate the role of "lethal cell" in determining disease status and therapy response of lung cancer patients. Univariate analysis of prognostic significance of "lethal cell" as described in Example I revealed that the lung cancer patients if associated with a lethal cell in tumor stroma and/or peripheral blood and/or ascites and/or pleural effusions and/or bone marrow tend to have very poor outcome ($P<0.001$). The 5-year disease-free survival for the patients with a lethal cell was 8.8% versus 68.4% for those patients without a lethal cell ($P<0.001$, FIG. 2A; Table 2) and the 5-year overall survival for the patients with a lethal cell was 15.0% versus 80.3% for the negative patients ($P<0.001$, FIG. 2B; Table 2).

TABLE 2

Univariate Analysis of Prognostic Factors for Disease-Free Survival and Overall Survival in 156 Lung Cancer Patients

|  |  | No. of patients | 5-Year Disease-Free Survival (%) | P* | 5-Year Overall Survival (%) | P* |
|---|---|---|---|---|---|---|
| Lethal cell | Negative | 76 | 68.4 | <0.001 | 80.3 | <0.001 |
|  | Positive | 80 | 8.8 |  | 15.0 |  |
| Gender | Male | 100 | 36.0 |  | 43.0 |  |
|  | Female | 56 | 41.1 | NS | 53.6 | NS |
| Smoking history | Nonsmoker | 84 | 39.3 |  | 52.4 |  |
|  | Smoker | 72 | 36.1 | NS | 40.3 | NS |
| Tumor size (cm) | ≦3 | 86 | 44.2 |  | 51.2 |  |
|  | >3 | 70 | 31.4 | 0.026 | 41.4 | 0.036 |
| CEA (ng/mL) | <3 | 54 | 42.6 |  | 51.9 |  |
|  | ≧3 | 32 | 43.8 | NS | 53.1 | NS |
| Histology | Adenocarcinoma | 117 | 36.8 |  | 47.0 |  |
|  | Squamous cell carcinoma | 36 | 44.4 |  | 50.0 |  |
|  | Large cell carcinoma | 3 | 0.0 | NS | 0.0 | 0.035 |
| Differentiation | Well | 42 | 45.2 |  | 57.1 |  |
|  | Moderately | 65 | 38.5 |  | 46.2 |  |
|  | Poorly | 49 | 30.6 | NS | 38.8 | NS |
| Depth of tumor invasion | T1 | 50 | 44.0 |  | 52.0 |  |
|  | T2 | 59 | 45.8 |  | 52.5 |  |
|  | T3 | 30 | 26.7 |  | 43.3 |  |
|  | T4 | 17 | 11.8 | 0.013 | 17.6 | 0.031 |

TABLE 2-continued

Univariate Analysis of Prognostic Factors for Disease-Free Survival and Overall Survival in 156 Lung Cancer Patients

|  |  | No. of patients | 5-Year Disease-Free Survival (%) | P* | 5-Year Overall Survival (%) | P* |
|---|---|---|---|---|---|---|
| Lymph node metastasis | N0 | 94 | 50.0 |  | 62.8 |  |
|  | N1 | 29 | 34.5 |  | 41.4 |  |
|  | N2 | 21 | 4.8 |  | 4.8 |  |
|  | N3 | 12 | 8.3 | <0.001 | 8.3 | <0.001 |
| Stage | I | 69 | 62.3 |  | 72.5 |  |
|  | II | 23 | 30.4 |  | 52.2 |  |
|  | III | 55 | 16.4 |  | 20.0 |  |
|  | IV | 9 | 0.0 | <0.001 | 0.0 | <0.001 |
| Postoperative adjuvant therapy | No | 82 | 59.8 |  | 65.9 |  |
|  | Yes | 74 | 13.5 | <0.001 | 25.7 | <0.001 |

Abbreviations:
CEA, carcinoembryonic antigen;
depth of tumor invasion (pT), pathological T status;
lymph node metastasis (pN), pathological N status;
NS, not statistically significant
*Log-rank test.

To evaluate the robustness of the prognostic value of lethal cell, Cox multivariate proportional hazards regression analysis was performed to derive risk estimates related to disease-free survival and overall survival with all the variables to control for confounders. Multivariate analysis (Table 3) showed that lethal cell and lymph node metastasis were the only two independent prognostic factors for the disease-free and overall survival. Lethal cell was found to be the strongest independent prognostic predictor for progression and patient survival of lung cancer (HR 5.575, 95% CI 3.502-8.875, P<0.001 for disease-free survival and HR 8.106, 95% CI 4.741-13.859, P<0.001 for overall survival).

TABLE 3

Cox Multivariate Regression Analysis of Potential Prognostic Factors for Disease-Free Survival and Overall Survival in 156 Lung Cancer Patients

|  | HR | 95% CI | P |
|---|---|---|---|
| Disease-free survival |  |  |  |
| Lethal cell |  |  |  |
| Positive vs. Negative | 5.575 | 3.502-8.875 | <0.001 |
| Lymph node metastasis |  |  |  |
| Positive vs. Negative | 2.036 | 1.356-3.056 | 0.001 |
| Overall survival |  |  |  |
| Lethal cell |  |  |  |
| Positive vs. Negative | 8.106 | 4.741-13.859 | <0.001 |
| Lymph node metastasis |  |  |  |
| Positive vs. Negative | 2.781 | 1.804-4.288 | <0.001 |

Abbreviations:
HR, hazard ratio,
95% CI, 95% confidence interval

Figure 3A:
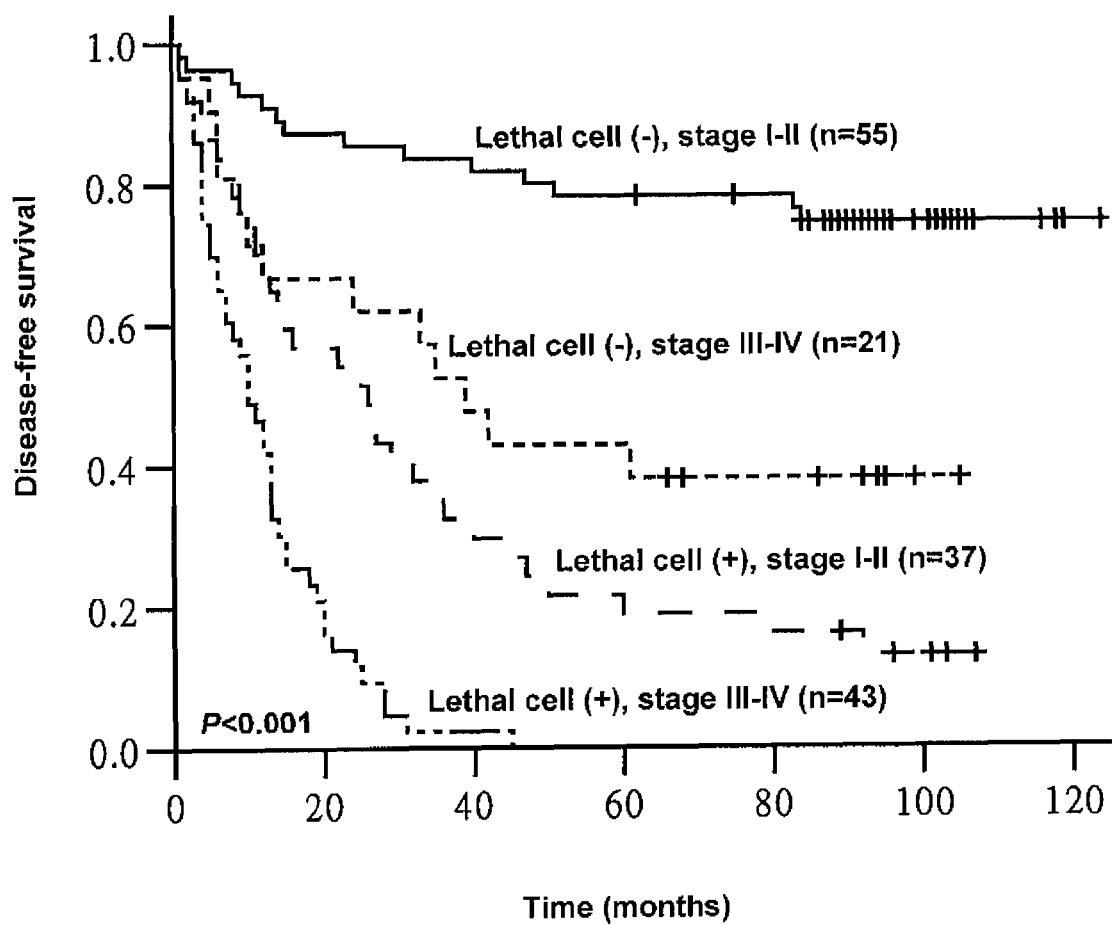
FIG. 3 depicts the disease-free and overall survival of lung cancer patients at all stage (A, B) or at stage I (C, D) with respect to lethal cell.
Figure 3B:
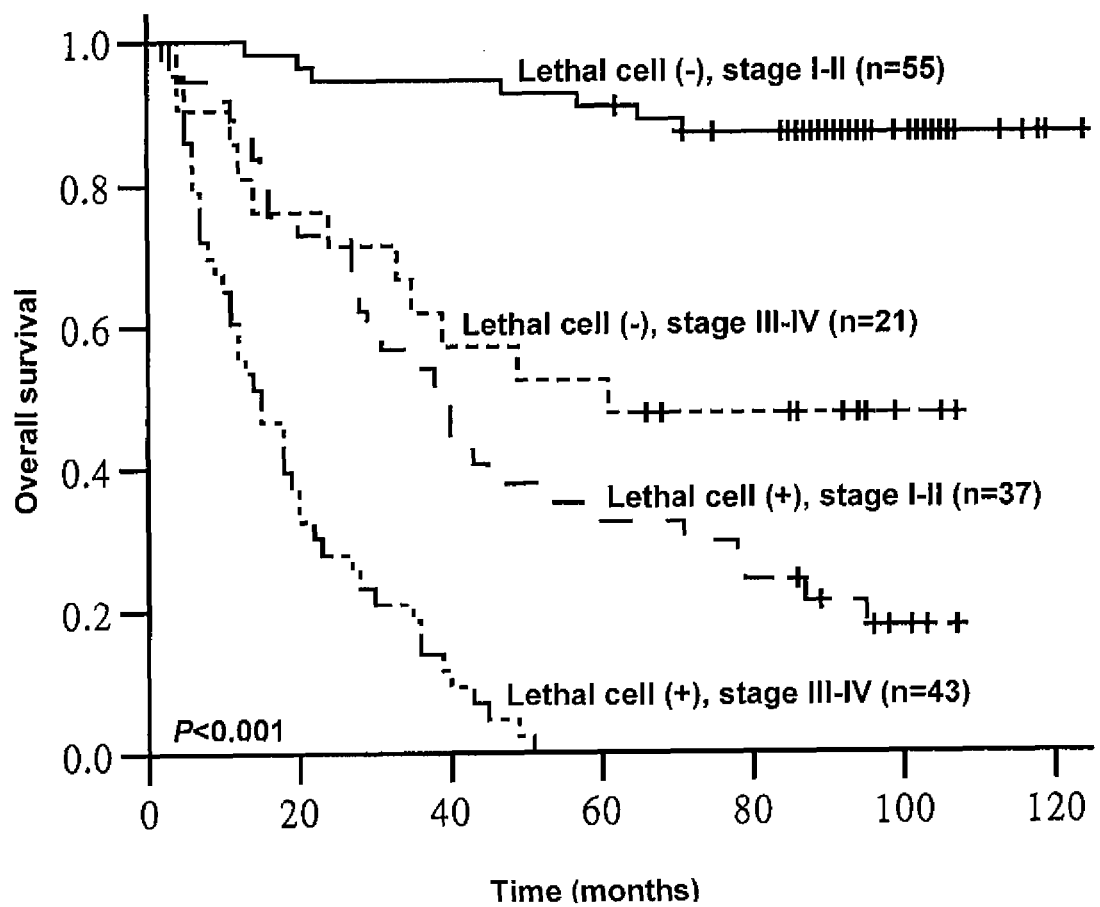
Figure 3C:
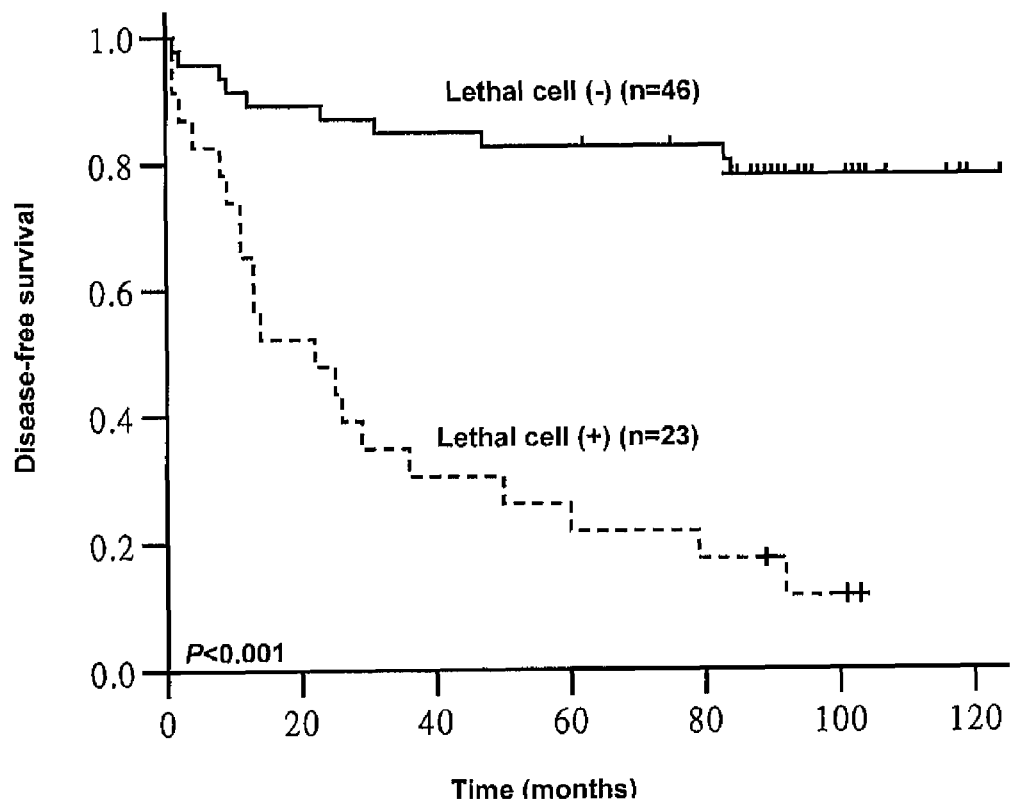
Figure 3D:
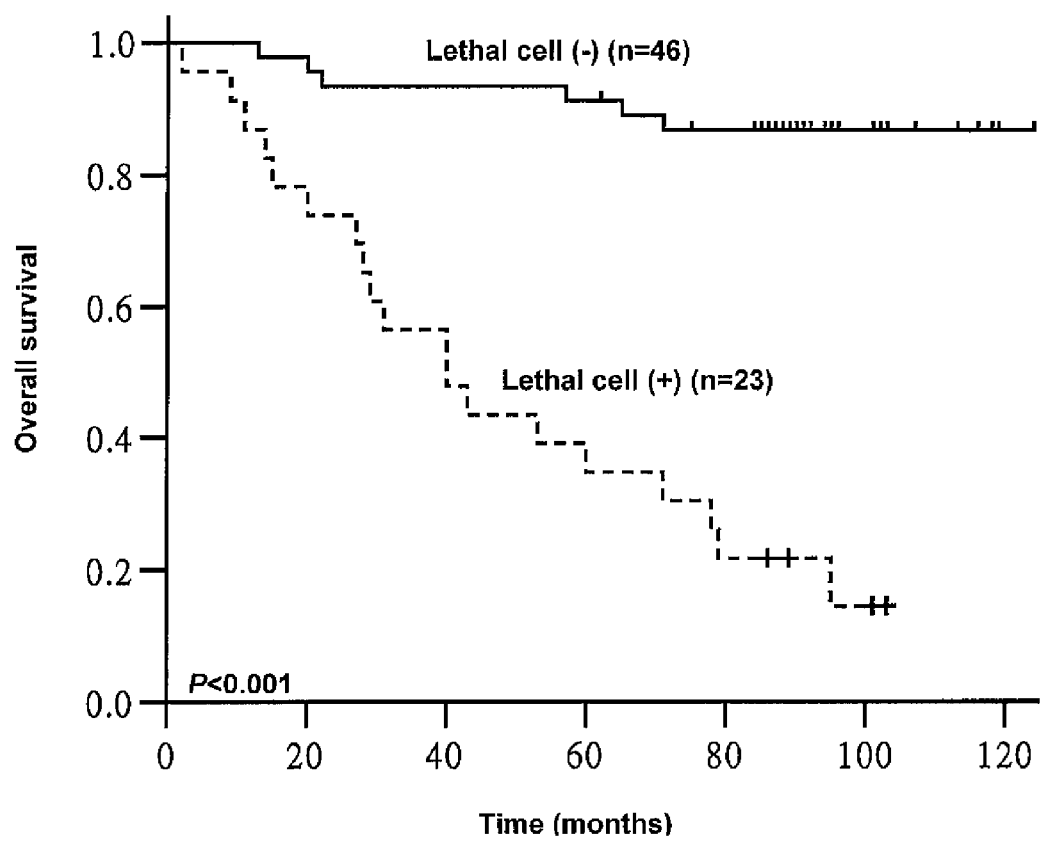

Moreover, of 92 early-stage patients, 37 patients (40.2%) exhibited a lethal cell and failed to have favorable outcome (FIGS. 3A and B). The early-stage patients with a lethal cell had more than 6-fold the risk of recurrence and more than 11-fold the risk of death compared with the early-stage patients without a lethal cell (HR 6.202, 95% CI 3.278-11.734 for disease-free survival and HR 11.112, 95% CI 4.854-25.440 for overall survival, P<0.001; Table 4). More specifically, of 69 stage-I patients, 46 patients (66.7%) were without a lethal cell and had very good outcome. In sharp contrast, the remaining 23 stage-I patients (33.3%) exhibited a lethal cell and failed to have favorable outcome (FIGS. 3C and D). The stage-I lung cancer patients if associated with a lethal cell had more than 7.5-fold the risk of relapse and more than 10.5-fold the risk of death compared with the same stage-I lung cancer patients but without any lethal cell (HR 7.736, 95% CI 3.596-16.643; P<0.001 for disease-free survival and HR 10.687, 95% CI 4.247-26.893; P<0.001 for overall survival). The hazard ratio of advanced-stage lung cancer patients if associated with a lethal cell even increased up to 35.2-fold. The detailed results were in Table 4.

TABLE 4

Cox Regression Analysis of Lethal cell and Independent Prognostic Factors for Disease-Free and Overall Survivals in 156 Lung Cancer Patients

|  | No. of patients | Disease-Free Survival | | | Overall Survival | | |
|---|---|---|---|---|---|---|---|
|  |  | HR | 95% CI | P | HR | 95% CI | P |
| LN status (−) |  |  |  |  |  |  |  |
| Lethal cell (−) | 54 | 1 |  | <0.001 | 1 |  | <0.001 |
| Lethal cell (+) | 40 | 5.627 | 3.092-10.239 | <0.001 | 8.878 | 4.232-18.626 | <0.001 |
| LN status (+) |  |  |  |  |  |  |  |
| Lethal cell (−) | 22 | 2.069 | 0.959-4.463 | 0.064 | 3.231 | 1.281-8.146 | 0.013 |
| Lethal cell (+) | 40 | 11.387 | 6.081-21.322 | <0.001 | 23.709 | 11.052-50.865 | <0.001 |
| Stage I-II |  |  |  |  |  |  |  |
| Lethal cell (−) | 55 | 1 |  | <0.001 | 1 |  | <0.001 |
| Lethal cell (+) | 37 | 6.202 | 3.278-11.734 | <0.001 | 11.112 | 4.854-25.440 | <0.001 |
| Stage III-IV |  |  |  |  |  |  |  |
| Lethal cell (−) | 21 | 3.546 | 1.662-7.563 | 0.001 | 6.257 | 2.421-16.174 | <0.001 |
| Lethal cell (+) | 43 | 16.507 | 8.505-32.037 | <0.001 | 35.216 | 15.117-82.038 | <0.001 |
| Stage I |  |  |  |  |  |  |  |
| Lethal cell (−) | 46 | 1 |  | <0.001 | 1 |  | <0.001 |
| Lethal cell (+) | 23 | 7.736 | 3.596-16.643 | <0.001 | 10.687 | 4.247-26.893 | <0.001 |

Abbreviations:
LN, lymph node metastasis;
HR, hazards ratio,
95% CI, 95% confidence interval It is interesting to note that of 74 patients subjected to postoperative adjuvant treatments, lethal cell was also significantly associated with patients' outcome. The lung cancer patients without lethal cell had much better outcome and the patients with a lethal cell predominantly had an evident worse outcome in response to adjuvant treatment and the 5-year survival for the positive patients was 12.0% versus 54.2% for the negative patients (P<0.001). When logistic regression was applied, lethal cell was found to be the most potential prognostic predictor of adjuvant treatment response in univariate analysis (Table 5). Multivariate analysis showed that lethal cell (P=0.002) and stage (P=0.024) were independent prognostic predictors of response to adjuvant therapy (Table 5). Lethal cell in lung cancer patients was further identified as the strongest independent prognostic indicator of adjuvant treatment response (OR 17.532, 95% CI 2.977-103.133, P=0.002; Table 5).

TABLE 5

Logistic Regression Analysis of Potential Prognostic Factors and Lethal cell as Predictors of Response to Adjuvant Therapy in 74 Lung Cancer Patients

|  |  | Univariate analysis | | | Multivariate analysis | | |
|---|---|---|---|---|---|---|---|
|  |  | OR for Survival | 95% CI | P | OR for Survival | 95% CI | P |
| Lethal cell | Negative | 11.190 | 2.701-46.367 | 0.001 | 17.523 | 2.977-103.133 | 0.002 |
|  | Positive | 1 |  |  | 1 |  |  |
| Smoking | Nonsmoker | 1.377 | 0.724-2.616 | NS | 0.187 | 0.026-1.328 | NS |
|  | Smoker | 1 |  |  |  |  |  |
| Gender | Male | 3.474 | 0.711-16.972 | NS | 1.695 | 0.204-14.062 | NS |
|  | Female | 1 |  |  |  |  |  |
| Age | ≦65 years | 1.912 | 0.539-6.787 | NS | 1.532 | 0.296-7.937 | NS |
|  | >65 years | 1 |  |  |  |  |  |
| Tumor size | <3 cm | 0.935 | 0.292-2.995 | NS | 0.470 | 0.089-2.466 | NS |
|  | ≧3 cm |  |  |  |  |  |  |
| Histology | AC | 0.551 | 0.145-2.097 | NS | 1.081 | 0.153-7.622 | NS |
|  | LCC, SCC | 1 |  |  |  |  |  |
| Differentiation | Well | 1.150 | 0.312-4.238 | NS | 0.397 | 0.059-2.657 | NS |
|  | Moderate, Poor | 1 |  |  |  |  |  |
| Depth of tumor invasion | T1-T2 | 0.780 | 0.226-2.693 | NS | — | — | — |
|  | T3-T4 | 1 |  |  |  |  |  |
| LN status | Negative | 1.321 | 0.396-4.411 | NS | — | — | — |
|  | Positive | 1 |  |  |  |  |  |

TABLE 5-continued

Logistic Regression Analysis of Potential Prognostic Factors and Lethal cell as Predictors of Response to Adjuvant Therapy in 74 Lung Cancer Patients

| | | Univariate analysis | | | Multivariate analysis | | |
|---|---|---|---|---|---|---|---|
| | | OR for Survival | 95% CI | P | OR for Survival | 95% CI | P |
| Stage | I-II | 3.469 | 0.960-12.538 | 0.058 | 9.731 | 1.354-69.942 | 0.024 |
| | III-IV | 1 | | | | | |

Abbreviations:
AC, adenocarcinoma;
LCC., large cell carcinoma;
SCC, squamous cell carcinoma;
depth of tumor invation (pT), pathological T status;
LN status (pN), lymph node metastasis (pathological N) status;
OR, odds ratio,
95% CI, 95% confidence interval;
NS, not statistically significant More than 30% of stage I lung cancer patients were found to be associated with a lethal cell and had poor therapy response and unfavorable outcome even after curative resections and/or systemic adjuvant therapy. On the other hand, relatively large populations of advanced stage lung cancer patients were found to be associated with a lethal cell and tend to have very unfavorable outcome and poor therapy response even after surgery and systemic adjuvant therapies. Lethal cell obviously plays a determinant and instructional role in determining a curable or incurable disease status and all kinds of therapy response of lung cancer patients at all stages. Thus, this invention provides methods and compositions for detection of lethal cell and uses thereof in lung cancer patients. The more aggressive and appropriate treatments definitely are needed to those lung cancer patients associated with a lethal cell. Targeting lethal cell should be as essential and critical as targeting conventional aggressive lung cancer cell in the treatment of lung cancer patients associated with a lethal cell.

Example III

Gastric Cancer Patients if Associated with a Lethal Cell Tend to have Very Unfavorable Outcome and Poor Therapy Response Gastric cancer is one of the leading causes of cancer-related deaths worldwide. The prognosis of the disease remains dismal despite technical advances in surgery and the use of adjuvant therapy. More than half of them will experience systemic metastasis within a few years after surgery occasionally, even in patients who undergo curative resection. Depth of tumor invasion and lymph node metastasis which were included in the tumor-node-metastasis staging system are widely used as guide for predicting prognosis. However, prognoses of patients with the same stage are heterogeneous. The poor prognosis is due to the lack of an effective rescue treatment modality. To establish new biological markers that may predict the natural history of the disease as a guide to treatment is urgently needed.

The study included a total of 146 patients with gastric cancer who had complete clinicopathologic data and specimen available for lethal cell study (Table 6). The clinicopathologic features of the patients studied were summarized in Table 6. Of 146 patients studied (94 male and 52 female) with ages ranging from 25 to 86 years (mean, 61.4 years), the average tumor size was 4.5±2.7 (mean±SD, median 4.0). Tumors located in cardic area in 20 patients (14%), body area in 48 patients (33%) and antrum area in 78 patients (53%). Lymphovascular invasion and lymph node metastasis were found in 76 patients (52%) and 81 patients (55%), respectively. Tumor cells invaded to mucosa (pT1) in 25 patients (17%), muscularis propria or subserosa (pT2) in 30 patients (21%), serosa (pT3) in 83 patients (57%), and adjacent organs (pT4) in 8 patients (5%). The gastric cancer patients were classified as stage I, II, III, and IV in 45 patients (31%), 25 patients (17%), 58 patients (40%) and 18 patients (12%), respectively. Histologic type based on Lauren classification was diffuse in 48 patients (33%), intestinal in 76 patients (52%) and mixed in 22 patients (15%). Surgery technique used was total gastrectomy in 44 patients (30%), subtotal gastrectomy in 96 patients (66%) and proximal gastrectomy in 6 patients (4%). Postoperative adjuvant chemotherapy was performed in 44 patients (30%). Five-year disease-free and overall survivals were 47.7% and 53.0%, respectively.

TABLE 6

The Gastric Cancer Patients Characteristics

| | | Case number | Percentage (%) |
|---|---|---|---|
| Age† | | 61.4 ± 12.5 | |
| Gender | Male | 94 | 64 |
| | Female | 52 | 36 |
| Tumor location | Cardia | 20 | 14 |
| | Body | 48 | 33 |
| | Antrum | 78 | 53 |
| Tumor size (cm)† | | 4.5 ± 2.7 | |
| Lymphovascular invasion | Absent | 70 | 48 |
| | Present | 76 | 52 |
| Depth of tumor invasion | pT1 | 25 | 17 |
| | pT2 | 30 | 21 |
| | pT3 | 83 | 57 |
| | pT4 | 8 | 5 |
| Lymph node metastasis | Absent | 65 | 45 |
| | Present | 81 | 55 |
| Tumor stage | I | 45 | 31 |
| | II | 25 | 17 |
| | III | 58 | 40 |
| | IV | 18 | 12 |
| Lauren classification | Diffuse | 48 | 33 |
| | Intestinal | 76 | 52 |
| | Mixed | 22 | 15 |
| Type of surgery | Proximal gastrectomy | 6 | 4 |
| | Subtotal gastrectomy | 96 | 66 |
| | Total gastrectomy | 44 | 30 |
| Chemotherapy | Not performed | 102 | 70 |
| | Performed | 44 | 30 |

TABLE 6-continued

The Gastric Cancer Patients Characteristics

|  |  | Case number | Percentage (%) |
|---|---|---|---|
| Lethal cell | Negative | 76 | 52.1 |
|  | Positive | 70 | 47.9 |

†The results of continuous variable are expressed as mean ± SD.

The patients characteristics in this study were similar to the current epidemiologic status, indicating that the results obtained from these cases in an independent cohort study are applicable to gastric cancer worldwide. It was therefore decided to use this representative study population to evaluate the role of lethal cell in determining disease status and therapy response of gastric cancer patients. Univariate analysis of prognostic significance of lethal cell by the Kaplan-Meier method revealed that the gastric patients if associated with a lethal cell tend to have very poor outcome (P<0.001). The 5-year disease-free survival for the patients with a lethal cell was 18.6% versus 74.7% for those patients without lethal cell (P<0.001) and the 5-year overall survival for the patients with a lethal cell was 20.6% versus 82.7% for the negative patients (P<0.001). Multivariate analysis showed that lethal cell (P<0.001), lymphovascular invasion (P<0.001) and serosa invasion (P=0.001) were independent prognostic factors for the disease-free survival. For the overall survival, lethal cell (P<0.001), lymphovascular invasion (P=0.002) and serosa invasion (P=0.002) were the independent prognostic factors. Lethal cell was found to be the strongest independent prognostic predictor for progression and patient survival of gastric cancer (HR 3.740, 95% CI 2.124-6.587, P<0.001 for disease-free survival and HR 5.409, 95% CI 2.858-10.238, P<0.001 for overall survival).

Several factors such as stage have been demonstrated as prognostic factors in previous studies. However, the prognoses with the similar clinicopathologic status are heterogeneous; thus, growing concern is focused on solving prognostic uncertainty (Table 7). Of 76 advanced-stage gastric cancer patients, 50 patients (65.8%) also exhibited a lethal cell and had very poor outcome (10.0% for 5-year disease-free survival and 10.6% for 5-year overall survival; P<0.001). In sharp contrast, of 70 early-stage patients, 20 patients (28.6%) surprisingly exhibited a lethal cell and failed to have favorable outcome (40.0% for 5-year disease-free survival and 45.0% for 5-year overall survival; P<0.001). The early-stage gastric cancer patients with a lethal cell had more than 9-fold the risk of recurrence and more than 16-fold the risk of death compared with the early-stage patients without lethal cell (HR 9.612, 95% CI 3.419-27.021 for disease-free survival and HR 16.540, 95% CI 4.703-58.171 for overall survival; P<0.001). The hazard ratio of advanced-stage gastric cancer patients if associated with a lethal cell even increased up to more than 40-fold. More specifically, the 5-year disease-free survival rate of the early-stage gastric cancer patients if associated with a lethal cell dramatically dropped from 92.0% to only 40.0% (P<0.001) compared with the same early-stage gastric cancer patients but without any lethal cell as determined by Kaplan-Meier survival curve and log-rank test. The 5-year disease-free survival rate of the advanced-stage gastric cancer patients if associated with a lethal cell even more dramatically dropped to only 10.0%. The detailed results were summarized in Table 7.

TABLE 7

Kaplan-Meier and Cox Regression Analysis of Lethal Cell and Stage for Disease-Free and Overall Survivals in 146 Patients with Gastric Cancer.

|  | No. of patients | Kaplan-Meier | | Cox regression | | |
|---|---|---|---|---|---|---|
|  |  | 5-year survival | P* | HR | 95% CI | P |
| Disease-free survival | | | | | | |
| Stage I-II | | | | | | |
| Lethal cells (−) | 50 | 92.0 | <0.001 | 1 |  | <0.001 |
| Lethal cells (+) | 20 | 40.0 |  | 9.612 | 3.419-27.021 | <0.001 |
| Stage III-IV | | | | | | |
| Lethal cells (−) | 26 | 40.6 |  | 9.360 | 3.423-25.600 | <0.001 |
| Lethal cells (+) | 50 | 10.0 |  | 25.086 | 9.838-63.966 | <0.001 |
| Overall survival | | | | | | |
| Stage I-II | | | | | | |
| Lethal cells (−) | 50 | 96.0 | <0.001 | 1 |  | <0.001 |
| Lethal cells (+) | 20 | 45.0 |  | 16.540 | 4.703-58.171 | <0.001 |
| Stage III-IV | | | | | | |
| Lethal cells (−) | 26 | 56.3 |  | 11.373 | 3.238-39.944 | <0.001 |
| Lethal cells (+) | 50 | 10.6 |  | 40.728 | 12.525-132.439 | <0.001 |

Abbreviations:
HR, hazard ratio,
95% CI, 95% confidence interval
*Log-rank test

It is interesting to note that of 44 patients subjected to postoperative adjuvant chemotherapy, lethal cell was also significantly associated with patients' outcome. The gastric cancer patients without lethal cell had much better outcome and the patients with a lethal cell predominantly had an evident worse outcome in response to adjuvant chemotherapy and the 5-year survival for the positive patients was 12.5% versus 50.0% for the negative patients (P<0.001). When logistic regression was applied, lethal cell in gastric cancer patients was further identified as the strongest independent prognostic indicator of adjuvant treatment response (OR for survival 34.575, 95% CI 2.841-420.835, P=0.005) in both univariate and multivariate analyses.

Lethal cell obviously plays a determinant and instructional role in determining a curable or incurable disease status and all kinds of therapy response of gastric cancer patients at all stages. Thus, this invention provides methods and compositions for detection of lethal cell and uses thereof in gastric cancer patients. The more aggressive and appropriate treatments definitely are needed to those gastric cancer patients associated with a lethal cell. Targeting lethal cell should be as essential and critical as targeting conventional aggressive gastric cancer cell in the treatment of gastric cancer patients associated with a lethal cell.

Example IV

Breast Cancer Patients if Associated with a Lethal Cell Tend to have Very Unfavorable Outcome and Poor Therapy Response Breast cancer is the most common cancer and second leading cause of cancer death among women. Management of patients is currently based on clinical and pathological characteristics; however, they may only partially reflect disease heterogeneity. More than 50% patients with poor outcome can not be identified by traditional prognostic markers. In fact, approximately one-third of node-negative patients and 60% of node-positive patients experience systemic relapse. The literatures suggest that several biomarkers may have prognostic significance in breast cancer. However, these factors are not sufficient for an accurate prediction of low-risk patients with no need for adjuvant therapy, and high-risk groups for systemic relapse. As it is not possible to accurately predict the risk of progression in individual patients, more than 80% of the breast cancer patients have received adjuvant therapy, although only a small proportion will benefit from this treatment. Therefore, more sensitive prognostic predictors are urgently needed to help identify low-risk and high-risk groups for disease progression and determine who will benefit from adjuvant therapy, which will enable oncologists to tailor treatment strategies to individual patients and simultaneously ensure the patients' life quality maintained.

There were 167 breast cancer patients who had complete clinicopathologic data and specimen available for lethal cell study. The clinicopathologic features of the patients studied were summarized in Table 8. Of 167 patients studied (all female) with ages ranging from 27 to 80 years (mean, 49.1 years), the average tumor size was 3.6±2.1 cm (mean±SD; median, 3.0 cm). The tumors were histologic grade 1 in 44 patients (26%), grade 2 in 72 patients (43%) and grade 3 in 51 patients (31%). There were 118 patients (71%) with lymph node metastasis. The cancer patients were classified as stage I, II, III, and IV in 21 patients (13%), 75 patients (45%), 65 patients (39%) and 6 patients (3%), respectively. PR positivity was detected in 70 patients (42%) whereas ER positivity was detected in 94 patients (56%). During the follow-up period, 30 patients (18%) experienced loco-regional recurrence and 55 patients (30.5%) experienced distant metastasis. Five-year survival of the 167 patients with breast cancer was 77.2%.

TABLE 8

The Breast Cancer Patients Characteristics

|  |  | Case number | Percentage (%) |
|---|---|---|---|
| Age (years)[†] | | 49.1 ± 10.1 | |
| Tumor size (cm)[†] | | 3.6 ± 2.1 | |
| Histologic grade | 1 | 44 | 26 |
| | 2 | 72 | 43 |
| | 3 | 51 | 31 |
| Lymph node status | Negative | 49 | 29 |
| | Positive | 118 | 71 |
| Stage | I | 21 | 13 |
| | II | 75 | 45 |
| | III | 65 | 39 |
| | IV | 6 | 3 |
| ER status | Negative | 65 | 39 |
| | Positive | 94 | 56 |
| PR status | Negative | 87 | 52 |
| | Positive | 70 | 42 |
| Recurrence | Absent | 137 | 82 |
| | Present | 30 | 18 |
| Metastasis | Absent | 112 | 67 |
| | Present | 55 | 33 |
| Hormone therapy | No | 50 | 30 |
| | Yes | 117 | 70 |
| Chemotherapy | No | 41 | 25 |
| | Yes | 126 | 75 |
| Adjuvant therapy | None | 9 | 5 |
| | Chemotherapy | 41 | 25 |
| | Hormone therapy | 32 | 19 |
| | Combined | 85 | 51 |
| Lethal cell | Negative | 119 | 71.3 |
| | Positive | 48 | 28.7 |

Abbreviations:
PR, progesterone receptor;
ER, Estrogen receptor
[†]The results of continuous variable are expressed as mean ± SD.

The patients characteristics in this study were similar to the current epidemiologic status, indicating that the results obtained from these cases in an independent cohort study are applicable to breast cancer worldwide. It was therefore decided to use this representative study population to evaluate the role of lethal cell in determining disease status and therapy response of breast cancer patients. Univariate analysis of prognostic significance of lethal cell by the Kaplan-Meier method revealed that the breast cancer patients with a lethal cell tend to have very poor outcome (P<0.001). The 5-year survival for the patients with a lethal cell was 54.2% versus 86.6% for those patients without lethal cell (P<0.001). Multivariate analysis showed that lethal cell (P<0.001), lymph node metastasis (P=0.016), tumor size (P<0.001) and ER status (P=0.005) were independent prognostic factors. Lethal cell was found to be the strongest independent prognostic predictor for patient survival of breast cancer (HR 6.033, 95% CI 3.324-10.950, P<0.001).

Moreover, of 96 early-stage breast cancer patients, 73 patients (76.0%) were also without lethal cell and had very good outcome (94.5% for 5-year overall survival; P<0.001). In sharp contrast, the remaining 23 (24.0%) early-stage patients surprisingly exhibited a lethal cell and failed to have favorable outcome (65.2% for overall survival; P<0.001). In similarity, of 75 stage II patients, 56 (74.7%) patients were also without lethal cell and had very good outcome (94.6% for 5-year overall survival; P<0.001). In sharp contrast, the remaining 19 (25.3%) stage II patients exhibited a lethal cell and failed to have favorable outcome (57.9% for 5-year overall survival; P<0.001).

The early-stage breast cancer patients if associated with a lethal cell had more than 13.5-fold the risk of death compared with the same early-stage breast cancer patients but without any lethal cell (HR 13.948, 95% CI 5.047-56.548; P<0.001).

The hazard ratio of advanced-stage breast cancer patients if associated with a lethal cell even increased to 19.434 (95% CI 7.210-52.319; P<0.001) as determined by Cox hazards regression analysis. More specifically, the Stage II breast cancer patients if associated with a lethal cell had more than 17-fold the risk of death compared with the same stage II breast cancer patients but without any lethal cell (HR 17.076, 95% CI 5.573-52.319; P<0.001). The multivariate logistic regression analysis further revealed that the breast cancer patients if not associated with any lethal cell retained the strongest independent role in response to chemotherapy with survival odds ratio up to 13.195-fold (95% CI 4.674-311.249; P<0.001) compared with the breast cancer patients associated with a lethal cell in response to chemotherapy. More specifically, the survival odds ratio of stage-II breast cancer patients if not associated with any lethal cell increased up to 22.688 (95% CI 4.841-106.315; P<0.001) compared with the same stage-II breast cancer patients but with a lethal cell in response to chemotherapy as determined by logistic regression analysis and the 5-year survival rate of the stage-II breast cancer patients with a lethal cell dropped from 91.9% to only 46.7% compared with the same stage-II breast cancer patients but with any lethal cell as determined by Kaplan-Meier survival curve and log-rank test. Likewise, the survival odds ratio of the stage-III breast cancer patients if not associated with any lethal cell increased up to 5.815 (95% CI 1.722-19.634) compared with the same stage-III breast cancer patients but with a lethal cell and the 5-year survival rate of the stage-III breast cancer patients with a lethal cell dropped from 75% to only 47.4% in response to chemotherapy.

Lethal cell obviously plays a determinant and instructional role in determining a curable or incurable disease status and all kinds of therapy response of breast cancer patients at all stages. Thus, this invention provides methods and compositions for detection of lethal cell and uses thereof in breast cancer patients. The more aggressive and appropriate treatments definitely are needed to those breast cancer patients associated with a lethal cell. Targeting lethal cell should be as essential and critical as targeting conventional aggressive breast cancer cell in the treatment of breast cancer patients associated with a lethal cell.

Example V

Prostate Cancer Patients if Associated with a Lethal Cell Tend to have Unfavorable Outcome and Poor Therapy Response Prostate cancer is the most common malignancy and the second leading cause of cancer death in males worldwide. Despite the availability of potential curative treatment including radical prostatectomy (RP) or radiotherapy for local treatment, many patients experience disease relapse after primary therapy. Clinical stage, Gleason's grade and prostate-specific antigen (PSA) level have been reported as prognostic factors and numerous molecular markers have been described in human serum, urine and seminal fluid. However, prostate cancer represents as a heterogeneous disease which can not be distinguished between aggressive and "indolent" tumors in an individual patient, a decision as to whether aggressive treatment should be used for patients still remains difficult. Therefore, prediction of the aggressiveness of prostate cancer to adopt the appropriate therapeutic modality for each individual is urgently needed.

There were 79 patients who had complete clinicopathologic data and specimen available for lethal cell study. The clinicopathologic features of the patients studied were summarized in Table 9. Of 79 patients studied with ages ranging from 46 to 95 years (mean, 71 years). The average pretreatment PSA level was 50.6±75.4 ng/mL (mean±SD; median, 23.2 ng/mL). A cutoff value of 7 was used to distinguish between low and high Gleason's grade and found in 36 patients (45.6%) and 43 patients (54.4%), respectively. The patients were classified as stage I, II, III, and IV in 9 patients (11.4%), 36 patients (45.6%), 10 patients (12.7%) and 24 patients (30.4%), respectively. The diagnostic material was obtained from primary tumor in 58 patients (73.4%) and recurrent tumor from 21 patients (26.6%). TURP was used for treating 21 patients (26.6%), TURP plus mixed treatment including radiotherapy, chemotherapy, and hormone therapy was used for treating 31 patients (39.2%), RP was used for treating 13 patients (16.5%) and RP plus mixed treatment including radiotherapy, chemotherapy, and hormone therapy was used for treating 14 patients (17.7%). During the follow-up period, 30 patients (38.0%) experienced disease relapse. Five-year survival of the 79 patients with prostate cancer was 77.0%.

TABLE 9

The Prostate Cancer Patients Characteristics

| | | Case number | % |
|---|---|---|---|
| Age (years)[†] | | 70.3 ± 8.3 | |
| PSA level (ng/ml)[†] | | 50.6 ± 75.4 | |
| Gleason's grade | <7 | 36 | 45.6 |
| | ≧7 | 43 | 54.4 |
| Clinical stage | I | 9 | 11.4 |
| | II | 36 | 45.6 |
| | III | 10 | 12.7 |
| | IV | 24 | 30.4 |
| Diagnostic material | Primary | 58 | 73.4 |
| | Recurrent | 21 | 26.6 |
| Therapy | TURP | 21 | 27.8 |
| | TURP + mixed treatment | 31 | 38.0 |
| | RP | 13 | 16.5 |
| | RP + mixed treatment | 14 | 17.7 |
| Disease relapse | No | 30 | 38.0 |
| | Yes | 49 | 62.0 |
| Lethal cell | Negative | 58 | 73.4 |
| | Positive | 21 | 26.6 |

Abbreviations:
PSA, prostate specific antigen;
TURP, transurethral resection of prostate;
RP, radical prostatectomy
[†]The results of continuous variable are expressed as mean ± SD.

The patients characteristics in this study were similar to the current epidemiologic status, indicating that the results obtained from these cases in an independent cohort study are applicable to prostate cancer worldwide. It was therefore decided to use this representative study population to evaluate the role of lethal cell in determining disease status and therapy response of prostate cancer patients. Univariate analysis of prognostic significance of lethal cell by the Kaplan-Meier method revealed that the prostate cancer patients if associated with a lethal cell tend to have poor outcome (P<0.001). The 5-year overall survival for the patients with a lethal cell was 61.5% versus 86.2% for those patients without lethal cell (P<0.001). Lethal cell was further identified as the strongest independent prognostic indicator for survival in prostate cancer patient subjected to transurethral resection of prostate (FIR 3.482, 95% CI 1.347-9.000, P=0.010).

More specifically, the 5-year survival of early-stage prostate cancer patients if associated with a lethal cell dramatically dropped from 97.1% (early-stage without lethal cell) to only 72.7%. In similarity, the 5-year survival of advanced-stage prostate cancer patients if associated with a lethal cell dropped from 70.8% (advanced stage without lethal cell) to only 40.0% (P<0.001; log-rank test). The multivariate Cox regression analysis further confirmed that the early-stage prostate cancer patients with a lethal cell had more than 6-fold the risk of poor outcome (HR6.178, 95% CI 1.445-19.832; P=0.013) compared with the same early-stage prostate cancer patients but without any lethal cell in response to radical prostatectomy and/or radiotherapy. The hazard ratio of advanced-stage prostate cancer patients if associated with a lethal cell increased to 24.340 (95% CI 6.415-92.349; P<0.001) in response to local radical prostatectomy, radiotherapy and systemic adjuvant therapy. The multivariate logistic regression analysis further established negative lethal cell as the strongest independent prognosticator of predicting survival odds of 45 patients subjected to systemic adjuvant therapy (OR 9.600, 95% CI 1.566-58.863; P=0.015). It is interesting note that the prostate cancer patients associated with both lethal cell and high PSA had more than 24-fold the risk of poor outcome compared with those prostate cancer patients without lethal cell and with low PSA. In similarity, the prostate cancer patients associated with both lethal cell and high Gleason's grade had more than 18-fold the risk of poor outcome compared with those prostate cancer patients without lethal cell and with low Gleason's grade (HR 18.214, 95% CI 3.872-85.690; P<0.001).

Lethal cell obviously plays a determinant and instructional role in determining a curable or incurable disease status and all kinds of therapy response of prostate cancer patients at all stages. Thus, this invention provides methods and compositions for detection of lethal cell and uses thereof in prostate cancer patients. The more aggressive and appropriate treatments definitely are needed to those prostate cancer patients associated with a lethal cell. Targeting lethal cell should be as essential and critical as targeting conventional aggressive prostate cancer cell in the treatment of prostate cancer patients associated with a lethal cell.

Example VI

Early-Stage Cervical Cancer Patients if Associated with a Lethal Cell Tend to have Unfavorable Outcome and Poor Therapy Response Cervical cancer is the second most common malignancy among women worldwide. Owning to increased availability of papanicolau smear screening programs, the frequent diagnosis of the disease is in its early stage. Surgery represents the mainstay of treatment for patients with early-stage cervical cancer. Nodal status is crucial for adjuvant treatment; however, it does not fully account for clinical outcomes. In fact, 10-15% of patients without lymph node involvement have tumor recurrence, and approximately half of patients with lymph node involvement are not cured after adjuvant treatment. Resistance to treatment and disease recurrences should be reliably predicted. Therefore, more accurate prognostic biomarkers strictly related to tumor aggressiveness are needed to help define a subgroup of patients at risk of recurrence and to individually tailor new treatment strategies for each patient.

The study included a total of 146 patients with early-stage cervical cancer who had complete clinicopathologic data and specimen available for lethal cell study in Table 10. Fourteen patients (9.6%) had stage IA disease, 112 patients (76.7%) had stage IB and 20 patients (13.7%) had stage IIA. The clinicopathologic features of the patients studied were summarized in Table 9. Of 146 cervical cancer patients studied with ages ranging from 22 to 86 years (mean, 50 years), the average tumor size was 2.4±1.4 cm (mean±SD; median, 2.0 cm). One hundred and twenty-four tumors (84.9%) were squamous cell carcinoma, although 14 tumors (9.6%) were adenocarcinoma and 8 tumors (5.5%) revealed an adenosquamous histotype. Lymphovascular and lymph node involvement were found in 43 patients (29.5%) and 28 patients (19.2%), respectively. The extents of differentiation in cervical cancer samples were graded as grade 1 in 58 patients (39.7%), grade 2 in 60 patients (41.1%) and grade 3 in 28 patients (19.2%). Fifty-nine patients (40.4%) received postoperative adjuvant therapy (43 patients received radiotherapy, 12 patients received both radiotherapy and chemotherapy and 4 patients received chemotherapy only). Five-year disease-free and overall survivals of the 146 patients with cervical cancer were 79.5% and 85.6%, respectively.

TABLE 10

The Cervical Cancer Patients Characteristics

|  |  | Case number | Percentage (%) |
|---|---|---|---|
| Age (years)† |  | 50 ± 10.9 | |
| Tumor Size (cm)† |  | 2.4 ± 1.4 | |
| Histotype | Squamous | 124 | 84.9 |
|  | Adenocarcinoma | 14 | 9.6 |
|  | Other | 8 | 5.5 |
| Grade | 1 | 58 | 39.7 |
|  | 2 | 60 | 41.1 |
|  | 3 | 28 | 19.2 |
| Parametrial Involvement | No | 129 | 88.4 |
|  | Yes | 17 | 11.6 |
| Lymphovascular Involvement | No | 103 | 70.5 |
|  | Yes | 43 | 29.5 |
| Lymph Node Involvement | No | 118 | 80.8 |
|  | Yes | 28 | 19.2 |
| Recurrent tumor | None | 121 | 82.9 |
|  | Pelvic | 14 | 9.6 |
|  | Pelvic and/or distant | 11 | 7.5 |
| Lethal cell | Negative | 129 | 88.4 |
|  | Positive | 17 | 11.6 |

†The results of continuous variable are expressed as mean ± SD.

The patients characteristics in this study were similar to the current epidemiologic status, indicating that the results obtained from these cases in an independent cohort study are applicable to early-stage cervical cancer worldwide. It was therefore decided to use this representative study population to evaluate the role of lethal cell in determining disease status and therapy response of early-stage cervical cancer patients. Univariate analysis of prognostic significance of lethal cell by the Kaplan-Meier method revealed that the cervical cancer patients if associated with a lethal cell tend to have poor outcome (P<0.001). The 5-year disease-free survival for the patients with a lethal cell was 42.1% versus 84.5% for those patients without lethal cell (P<0.001) and the 5-year overall survival for the patients with a lethal cell was 41.2% versus 91.5% for the negative patients (P<0.001). Multivariate analysis showed that lethal cell (P<0.001) and lymph node involvement (P<0.001) were independent prognostic factors for the disease-free survival. For the overall survival, lethal cell (P<0.001) and lymph node involvement (P<0.001) were also the only two independent prognostic factors. Lethal cell was found to be the strongest independent prognostic predictor for progression and patient survival of early-stage cervical cancer (HR 8.533, 95% CI 3.794-19.190, P<0.001 for disease-free survival and HR 9.678, 95% CI 3.997-23.434, P<0.001 for overall survival).

Of 59 patients subjected to postoperative adjuvant treatments, lethal cell was significantly associated with patients' outcome. The early-stage cervical cancer patients without lethal cell had much better outcome and the patients with a lethal cell predominantly had an evident worse outcome in response to adjuvant treatment and the 5-year survival for the patients with a lethal cell was 14.3% versus 80.8% for those patients without lethal cell (P<0.001). When logistic regression was applied, lethal cell (P=0.008), grade (P=0.045) and lymph node involvement (P=0.015) were potential prognostic predictors of therapy response in univariate analysis. Multivariate analysis showed that lethal cell (P=0.006) and lymph node involvement (P=0.034) were independent prognostic predictors of response to adjuvant therapy. Lethal cell in early-stage cervical cancer was identified as the strongest independent prognostic indicator of adjuvant therapy response (OR 34.636, 95% CI 2.786-430.543, P=0.006).

Lethal cell obviously plays a determinant and instructional role in determining a curable or incurable disease status and all kinds of therapy response of cervical cancer patients. Thus, this invention provides methods and compositions for detection of lethal cell and uses thereof in cervical cancer patients. The more aggressive and appropriate treatments definitely are needed to those early-stage cervical cancer patients associated with a lethal cell. Targeting lethal cell should be as essential and critical as targeting conventional aggressive early-stage cervical cancer cell in the treatment of early-stage cervical cancer patients associated with a lethal cell.

Example VII

Colorectal Cancer Patients if Associated with a Lethal Cell Tend to have Unfavorable Outcome and Poor Therapy Response Colorectal cancer is the second most common cancer in the world and the third most common cause of cancer-related death. Despite major advances have been achieved concerning the molecular pathogenesis of colorectal cancer, therapeutic options are still unsatisfactory. Tumor stage at diagnosis is still the most important clinicopathological indicator of prognosis. However, patients with a similar pathological disease stage can exhibit varying survival outcomes. For example, the inaccuracy of determining the prognosis of patients with Stage II-III disease may be as high as 40%. This can lead to extreme difficulty in choosing the correct adjuvant treatment protocol and may also lead to overtreatment or undertreatment in many patients. Therefore, new strategies to better predict the outcome and for risk-adapted therapies are warranted.

There were 74 patients who had complete clinicopathologic data and specimen available for lethal cell study. The clinicopathologic features of the patients studied were summarized in Table 11. Of 74 colorectal cancer patients studied (37 male and 37 female) with ages ranging from 27 to 97 years (mean, 63 years), the average tumor size was 5.0±2.8 cm (mean±SD; median, 4.5 cm), and the primary sites of the tumors were classified as colon in 59 patients (79.7%) and rectum in 15 patients (20.3%). The extents of differentiation in colorectal cancer samples were graded as well-differentiated in 7 patients (9.5%), moderately-differentiated in 61 patients (82.4%), and poorly-differentiated in 6 patients (8.1%). The cancer patients were classified as stage I, II, III, and IV in 9 patients (12.2%), 40 patients (54.1%), 18 patients (24.3%), and 7 patients (9.5%), respectively. The depth of invasion was assessed and recorded as T1, T2, T3, and T4 in 2 patients (2.7%), 8 patients (10.8%), 13 patients (17.6%), and 51 patients (68.9%), respectively. Fifty patients (67.6%) had positive pathologic N status, whereas 24 patients (32.4%) did not. Thirty five (47.3%) of the 74 patients had received adjuvant therapy. By 2005, cutoff date for follow-up, 50 patients (67.6%) were alive, and 24 patients (32.4%) had died of disease. Five-year disease-free survival and overall survival of the 74 patients with colorectal cancer were 67.5% and 70.2%, respectively.

TABLE 11

The Colorectal Cancer Patients Characteristics

| | | Case number | Percentage (%) |
|---|---|---|---|
| Age (years)† | | 63.5 ± 13.5 | |
| Tumor size (cm)† | | 5.0 ± 2.8 | |
| Gender | Male | 37 | 50.0 |
| | Female | 37 | 50.0 |
| Grade of differentiation | Well | 7 | 9.5 |
| | Moderate | 61 | 82.4 |
| | Poor | 6 | 8.1 |
| Location | Colon | 59 | 79.7 |
| | Rectum | 15 | 20.3 |
| Tumor invasion | pT1 | 2 | 2.7 |
| | pT2 | 8 | 10.8 |
| | pT3 | 13 | 17.6 |
| | pT4 | 51 | 68.9 |
| Lymph node metastasis | Negative | 50 | 67.6 |
| | Positive | 24 | 32.4 |
| Tumor stage, TNM | I | 9 | 12.2 |
| | II | 40 | 54.1 |
| | III | 18 | 24.3 |
| | IV | 7 | 9.4 |
| Recurrence | None | 61 | 82.4 |
| | Distant | 11 | 14.9 |
| | Distant and Local | 2 | 2.7 |
| Postoperative adjuvant therapy | No | 39 | 52.7 |
| | Yes | 35 | 47.3 |
| | Chemotherapy | 27 | |
| | Radiotherapy | 2 | |
| | Both Chemo-/Radiotherapy | 6 | |
| Lethal cell | Negative | 48 | 64.9 |
| | Positive | 26 | 35.1 |

†The results of continuous variable are expressed as mean ± SD.

The patients characteristics in this study were similar to the current epidemiologic status, indicating that the results obtained from these cases in an independent cohort study are applicable to colorectal cancer worldwide. It was therefore decided to use this representative study population to evaluate the role of lethal cell in determining disease status and therapy response of colorectal cancer patients. Univariate analysis of prognostic significance of lethal cell by the Kaplan-Meier method revealed that the colorectal cancer patients if associated with a lethal cell tend to have poor outcome (P<0.001). The 5-year disease-free survival for the patients with a lethal cell was 42.3% versus 81.2% for the negative patients (P<0.001) and the 5-year overall survival for the patients with a lethal cell was 46.2% versus 83.2% for the negative patients (P<0.001). Multivariate analysis showed that lethal cell (P=0.003) and lymph node metastasis (P=0.040) were the independent prognostic factors for the disease-free survival. For the overall survival, lethal cell (P=0.005) and lymph node metastasis (P=0.024) were also the only independent prognostic factors. Lethal cell was found to be the strongest independent prognostic predictor for progression and patient survival of colorectal cancer (HR 4.279, 95% CI 1.647-11.114, P=0.003 for disease-free survival and HR 4.306, 95% CI 1.557-11.909, P=0.005 for overall survival).

More specifically, the stage II-III colorectal cancer patients if associated with a lethal cell tend to have poor outcome after adjuvant chemotherapy. The 5-year survival rate of the stage II-III colorectal cancer patients with a lethal cell dramatically dropped from 77.3% to only 38.5% (P<0.001) compared with the same stage II-III colorectal cancer patients but without any lethal cell in response to adjuvant chemotherapy as determined by Kaplan-Meier survival curve and log-rank test. The logistic regression analysis further revealed that the survival odds ratio of the stage II-III colorectal cancer patients without any lethal cell increased up to 5.440 (95% CI 1.217-24.321; P=0.027) compared with the same stage II-III colorectal cancer patients but with a lethal cell in response to adjuvant chemotherapy.

Lethal cell obviously plays a determinant and instructional role in determining a curable or incurable disease status and all kinds of therapy response of colorectal cancer patients at all stages. Thus, this invention provides methods and compositions for detection of lethal cell and uses thereof in colorectal cancer patients. The more aggressive and appropriate treatments definitely are needed to those colorectal cancer patients associated with a lethal cell. Targeting lethal cell should be as essential and critical as targeting conventional aggressive colorectal cancer cell in the treatment of colorectal cancer patients associated with a lethal cell.

Example VIII

Pancreatic Cancer Patients if Associated with a Lethal Cell Tend to have Very Unfavorable Outcome and Poor Therapy Response Pancreatic cancer is the fourth leading cause of cancer death and has the lowest survival rate for any solid cancer. Due to its late discovery, rapid progression and resistance to chemo- and radiotherapy, pancreatic cancer is an extremely life-threatening neoplasm. For those patients that undergo potentially curative resection, the 5-year survival is only 20%. Because in its early stages, it is not always an easy diagnosis to make, many investigators over the years have sought to find accurate markers of pancreatic cancer. The current standard serum marker, sialylated Lewis (a) blood group antigen CA19-9, is widely used, but it is unable to reliably differentiate patients with extremely malignant behavior. Thus, there is a great need for multisubstrate/multifunctional signaling molecules to facilitate a better understanding of the molecular etiology of pancreatic cancer and provide the potential target to develop novel screening and early diagnostic and therapeutic strategies.

The study included a total of 74 patients with pancreatic cancer who had complete clinicopathologic data and specimen available for lethal cell study. The clinicopathologic features of the patients studied were summarized in Table 12. Of 74 patients studied (48 male and 26 female) with ages ranging from 36 to 80 years (mean, 61.8 years), the average tumor size was 4.4±1.9 (mean±SD, median 4.0). Tumors located in head area in 56 patients (75.7%) and body or tail area in 18 patients. Lymphovascular invasion and lymph node metastasis were found in 35 patients (47.3%) and 39 patients (52.7%), respectively. According to the staging system of 2002, the depth of tumor invasion was pT2 in 17 patients (23.0%), pT3 in 43 patients (51.4%) and pT4 in 13 patients (24.3%). As according to 2002 staging system, the patients was classified as stage I in 10 patients (13.5%), stage II in 40 patients (54.1%), stage III in 11 patients (14.9%), and stage IV in 13 patients (17.6%). Perineural invasion was observed in 40 patients (54.1%). The tumor differentiation was graded as well in 18 patients (24.3%), moderate in 38 patients (51.4%) and poor in 18 patients (24.3%). The adjuvant therapy was performed in 27 patients (36.5%). Two-year disease-free and overall survivals were 18.6% and 28.9%, respectively.

TABLE 12

The Pancreatic Cancer Patients Characteristics

|  |  | Case number | Percentage (%) |
|---|---|---|---|
| Age[†] |  |  | 61.8 ± 11.1 |
| Gender | Male | 48 | 64.9 |
|  | Female | 26 | 35.1 |
| Tumor location | Head | 56 | 75.7 |
|  | Body/tail | 18 | 24.3 |
| Tumor size (cm)[†] |  |  | 4.4 ± 1.9 |
| CA19-9 | <37 | 25 | 33.8 |
|  | ≧37 | 49 | 66.2 |
| Depth of tumor invasion | pT2 | 17 | 23.0 |
|  | pT3 | 43 | 51.4 |
|  | pT4 | 13 | 24.3 |
| Lymph node metastasis | Absent | 33 | 44.6 |
|  | Present | 38 | 51.4 |
| Tumor stage | I | 10 | 13.5 |
|  | II | 40 | 54.1 |
|  | III | 11 | 14.9 |
|  | IV | 13 | 17.6 |
| Lymphovascular invasion | Absent | 39 | 52.7 |
|  | Present | 35 | 47.3 |
| Perineural invasion | Absent | 34 | 45.9 |
|  | Present | 40 | 54.1 |
| Differentiation | Well | 18 | 24.3 |
|  | Moderate | 38 | 51.4 |
|  | Poor | 18 | 24.3 |
| Adjuvant therapy | Not performed | 47 | 63.5 |
|  | Performed | 27 | 36.5 |
| Disease relapse | No | 15 | 20.3 |
|  | Yes | 59 | 79.7 |
| Lethal cell | Negative | 20 | 27.0 |
|  | Positive | 54 | 73.0 |

[†]The results of continuous variable are expressed as mean ± SD.

The patients characteristics in this study were similar to the current epidemiologic status, indicating that the results obtained from these cases in an independent cohort study are applicable to pancreatic cancer worldwide. It was therefore decided to use this representative study population to evaluate the role of lethal cell in determining disease status and therapy response of pancreatic cancer patients. Univariate analysis of prognostic significance of lethal cell by the Kaplan-Meier method revealed that the pancreatic cancer patients if associated with a lethal cell tend to have very poor outcome (P<0.001). The 2-year disease-free survival for the patients with a lethal cell was 5.5% versus 51.5% for those patients without lethal cell (P<0.001) and the 2-year overall survival for the patients with a lethal cell was 13.3% versus 67.6% for the negative patients (P<0.001). Multivariate analysis showed that lethal cell (P=0.001), tumor location (P=0.004), lymph node metastasis (P=0.018) and CA 19-9 (P=0.041) were independent prognostic factors for the disease-free survival. For the overall survival, lethal cell (P=0.001), tumor location (P=0.001) and CA 19-9 (P=0.012) were the independent prognostic factors. Lethal cell was found to be the strongest independent prognostic predictor for progression and patient survival of pancreatic cancer (HR 4.309, 95% CI 1.890-9.821, P=0.001 for disease-free survival and HR 4.844, 95% CI 1.831-12.816, P=0.001 for overall survival).

More specifically, more than 58% of early-stage pancreatic cancer patients exhibited a lethal cell and failed to have favorable outcome (17.1% vs. 70.0% for 2-year disease-free survival and 15.6% vs. 80.0% for 2-year overall survival; P<0.001). The early-stage pancreatic cancer patients if associated with a lethal cell obviously had an evident worse outcome even after potentially curative treatments compared with the same early-stage pancreatic cancer patients but without any lethal cell. The logistic regression analysis further revealed that the pancreatic cancer patients if associated with a lethal cell tend to have poor response to adjuvant therapy. The 2-year survival of pancreatic cancer patients was only 12.5% vs. 66.7% for the lethal cell-negative pancreatic cancer patients and the odds ratio of the lethal cell-negative patients was more than 14-fold compared with the positive patients in response to adjuvant therapy (OR 14.250, 95% CI 1.162-174.801; P=0.038)

Lethal cell obviously plays a determinant and instructional role in determining a curable or incurable disease status and all kinds of therapy response of pancreatic cancer patients at all stages. Thus, this invention provides methods and compositions for detection of lethal cell and uses thereof in pancreatic cancer patients. The more aggressive and appropriate treatments definitely are needed to those pancreatic cancer patients associated with a lethal cell. Targeting lethal cell should be as essential and critical as targeting conventional aggressive pancreatic cancer cell in the treatment of pancreatic cancer patients associated with a lethal cell.

Example IX

Bile Duct Cancer Patients if Associated with a Lethal Cell Tend to have Very Unfavorable Outcome and Poor Therapy Response Cancer of the bile duct is the second most common primary hepatic tumor. The worldwide incidence of bile duct has risen over the past three decades. Surgery remains the only intervention offering the possibility of a cure. Unfortunately, the prognosis of patients with bile duct cancer is usually frustrated despite recent advances in surgical and medical treatments. Several factors have been demonstrated as prognostic factors such as lymph node metastasis and histological grade. However, the prognoses with the similar clinicopathologic status are heterogeneous. Therefore, there is intense interest in gaining a better understanding of the molecular and cellular processes involved in bile duct cancer to develop more reliable biomarkers to predict poor outcome of patients with particularly aggressive disease for optimal medical management. However, the molecular and cellular action mechanisms for tumor aggressiveness and the progression of bile duct cancer remain largely unclear and need to be further established.

There were 121 early-stage bile duct cancer patients who had complete clinicopathologic data and specimen available for lethal cell study. The clinicopathologic features of the patients studied were summarized in Table 13. Of 121 bile duct cancer patients studied (52 male and 69 female) with ages ranging from 25 to 89 years (mean, 63.2 years), the average tumor size was 3.4±1.9 cm (mean±SD; median, 3 cm). According to its location in the biliary tree, the tumors were classified into intrahepatic and extrahepatic types in 56 patients (46.3%) and 65 patients (53.7%), respectively. The extents of differentiation were graded as well-differentiated in 36 patients (29.7%), moderately-differentiated in 59 patients (48.8%) and poorly-differentiated in 26 patients (21.5%). The tumor was confined to the bile duct (T1) in 43 patients (35.5%), invades beyond the wall of the bile duct (T2) in 25 patients (20.7%) and invades the liver, gallbladder, pancreas and/or unilateral branches of the portal vein or hepatic artery (T3) in 53 patients (43.8%). There were 91 patients (75.2%) without lymph node metastasis. The early-stage bile duct cancer patients were classified as stage I and II in 58 patients (47.9%) and 63 patients (52.1%), respectively. Five-year survival of the 121 early-stage bile duct cancer patients was 32.7%.

TABLE 13

The Bile Duct Cancer Patients Characteristics

| | | Case number | Percentage (%) |
|---|---|---|---|
| Lethal cells | Negative | 46 | 38.0 |
| | Positive | 75 | 62.0 |
| Age[†] | | 63.2 ± 12.5 | |
| Gender | Male | 52 | 43.0 |
| | Female | 69 | 57.0 |
| Tumor size[†] | | 3.4 ± 1.9 | |
| Tumor location | Intrahepatic | 56 | 46.3 |
| | Extrahepatic | 65 | 53.7 |
| Differentiation | Well | 36 | 29.7 |
| | Moderate | 59 | 48.8 |
| | Poor | 26 | 21.5 |
| Depth of tumor invasion | T1 | 43 | 35.5 |
| | T2 | 25 | 20.7 |
| | T3 | 53 | 43.8 |
| Lymph node metastasis | Negative | 91 | 75.2 |
| | Positive | 30 | 24.8 |
| Stage | I | 58 | 47.9 |
| | II | 63 | 52.1 |

[†]The results of continuous variables are expressed as mean ± SD.

The patients characteristics in this study were similar to the current epidemiologic status, indicating that the results obtained from these cases in an independent cohort study are applicable to bile duct cancer worldwide. It was therefore decided to use this representative study population to evaluate the role of lethal cell in determining disease status and therapy response of bile duct cancer patients. Kaplan-Meier survival curve and log-rank test revealed that 75 of 121 (62.0%) early-stage bile duct cancer patients exhibited a lethal cell and had very poor outcome. The 5-year survival of early-stage bile duct cancer patients if associated with a lethal cell dropped from more than 65% to less than 20% compared with the same early-stage bile duct cancer patients but without any lethal cell (P<0.001, log-rank test). The median survival was 14 months for the patients with lethal cell vs. not reached for those without lethal cell (P<0.001). Cox regression analysis also confirmed that the early-stage bile duct cancer patients if associated with a lethal cell had more than 3-fold the risk of poor outcome compared with the same early-stage bile duct cancer patients but without any lethal cell (Hazard ratio 3.262, 95% CI 1.806-5.889; P<0.001). Moreover, there were another 29 advanced-stage bile duct cancer patients who had complete clinicopathologic data and specimen available for lethal cell study. It is interesting to note that of 29 advanced stage patients, 25 (86.2%) patients also exhibited a lethal cell and had very poor outcome. The 2-year survival rate for the advanced-stage bile duct cancer patients associated with a lethal cell is less than 5% and the median survival was 7.2 months.

Lethal cell obviously plays a determinant and instructional role in determining a curable or incurable disease status and all kinds of therapy response of bile duct cancer patients at all stages. Thus, this invention provides methods and compositions for detection of lethal cell and uses thereof in bile duct cancer patients. The more aggressive and appropriate treatments definitely are needed to those bile duct cancer patients associated with a lethal cell. Targeting lethal cell should be as essential and critical as targeting conventional aggressive bile duct cancer cell in the treatment of bile duct cancer patients associated with a lethal cell.

Example X

Kidney Cancer Patients if Associated with a Lethal Cell Tend to have Very Unfavorable Outcome and Poor Therapy Response Kidney cancer accounts for 3% of all malignancies in man and is the third most common urological cancer after prostate and bladder cancer. To date, tumor stage and grade have been considered the major prognostic parameters for patients with kidney cancer. However, in many cases, these parameters were insufficient to predict the clinical behavior of kidney tumors. Recent studies also demonstrated that stage alone cannot be relied on to predict tumor recurrence in localized cases. So, resection of kidney is the main treatment for kidney cancer but effective only in about 70% of early-stage and localized kidney cancer. Therefore, additional prognostic factors are needed to identify patients at high risk of tumor progression.

There were 88 kidney cancer patients who had complete clinicopathologic data and specimen available for lethal cell study. The clinicopathologic features of the patients studied were summarized in Table 14. There were 52 men and 36 women who underwent nephrectomy in the study, ranging from 31 to 73 years of age (medium, 59 years). The mean size of tumors was 7.0±4.7 cm. Among the 88 tumors examined, 71 tumors (80.7%) were conventional (clear cell carcinoma), 5 tumors (5.7%) were papillary renal carcinoma, 4 tumors (4.5%) were mixed renal carcinoma, 1 tumors (1.1%) were collecting duct renal carcinoma, and 7 tumors (7.9%) were unclassified renal cell carcinoma. The grading distribution was as follows: 29 (33.0%) grade 1, 32 (36.4%) grade 2, 16 (18.2%) grade 3, and 11 (12.5%) grade 4 tumors. Tumor stage was defined according to the tumor-node-metastasis (TNM) classification. There were 59 (67.0%) tumors limited to the kidney (stage I-II) and 21 (23.9%) tumors that expanded outside the kidney (stage III-IV). At the time of surgery, 4 patients had distant metastases. Survival time was calculated from the date of surgery to the date of death or to the date of the last follow up. year overall survival for the patients with a lethal cell was 53.3% versus 93.1% for the negative patients ($P<0.001$). Multivariate analysis showed that lethal cell ($P<0.001$) and lymph node metastasis ($P<0.001$) were independent prognostic factors for the disease-free survival. For the overall survival, lethal cell ($P<0.001$) and lymph node metastasis ($P=0.001$) were also the only independent prognostic factors. Lethal cell was found to be the strongest independent prognostic predictor for progression and patient survival of kidney cancer (HR, 4.307; 95% CI, 2.068 to 8.969 for disease-free survival, $P<0.001$ and HR, 8.359; 95% CI, 2.659 to 26.272 for overall survival; $P<0.001$).

More specifically, the 5-year disease-free survival rate of early-stage kidney cancer patients if associated with a lethal cell dropped from 86.4% to only 40.0% ($P<0.001$) compared with the same early-stage kidney cancer patients but without any lethal cell as determined by Kaplan-Meier survival curve and log-rank test. In advanced-stage kidney cancer patients, the 5-year disease-free survival of lethal cell-positive patients was only 20.0% versus 54.5% for the lethal cell-negative patients. The Cox hazard regression analysis further revealed that the early-stage kidney cancer patients had more than 3.5-fold the risk of relapse compared with the same early-stage kidney cancer patients but without any lethal cell (HR 3.547, 95% CI 1.493-8.424; $P=0.004$) and the hazard ratio of advanced-stage kidney cancer patients increased to 8.974 (95% CI 3.667-21.961; $P<0.001$). The logistic regression analysis also confirmed that the kidney cancer patients held the survival odds ratio of 8.320 (95% CI 1.972-35.009; $P=0.004$) if not associated with a lethal cell in response to surgery and adjuvant therapy.

Lethal cell obviously plays a determinant and instructional role in determining a curable or incurable disease status and all kinds of therapy response of kidney cancer patients at all stages. Thus, this invention provides methods and compositions for detection of lethal cell and uses thereof in kidney cancer patients. The more aggressive and appropriate treatments definitely are needed to those kidney cancer patients associated with a lethal cell. Targeting lethal cell should be as essential and critical as targeting conventional aggressive kidney cancer cell in the treatment of kidney cancer patients associated with a lethal cell.

Example XI

Brain Cancer Patients if Associated with a Lethal Cell Tend to have Very Unfavorable Outcome and Poor Therapy Response Brain cancer is the most common tumors of the central nervous system and are comprised of different forms. Despite the growing amount of information regarding the molecular, biochemical, and morphologic characteristics of brain cancer, the success of their treatment remains limited. To date, only age and histologic grade stand out as independent predictors of survival. While within each tumor grade, the clinical course is still variable because of the fact that each grade of tumor is not a single pathological entity but encompasses a spectrum of tumors with variable malignant potential. Therefore, to identify new biologic markers is crucial to the development of more effective therapeutic approaches, predicting responses to treatment, and improving survival rates.

There were 81 brain cancer patients who had complete clinicopathologic data and specimen available for lethal cell study. The clinicopathologic features of the patients studied were summarized in Table 15. Of 81 patients studied (41 male and 40 female) with ages ranging from 3 to 77 years (mean, 42 years), the average tumor size was 4.7±2.3 cm (mean±SD; median, 4.0 cm). Tumor samples were graded using the World Health Organization criteria: 28 (35%) tumors were classified as low-grade astrocytomas (Grade 2), 14 (17%) anaplastic or oligoastrocytoma (Grade 3), and 39 (48%) glioblastoma multiform (Grade 4). Fifty patients (61.7%) received postoperative irradiation and/or chemotherapy. Five-year disease-free survival and overall survival of the 81 patients were 28.2% and 40.6%, respectively.

TABLE 15

The Brain Cancer Patients Characteristics

|  |  | Case number | Percentage (%) |
|---|---|---|---|
| Age (years)[†] |  | 41.5 ± 118.8 |  |
| Tumor size (cm)[†] |  | 4.7 ± 2.3 |  |
| Gender | Male | 41 | 51 |
|  | Female | 40 | 49 |
| Histology (WHO grade) | Low grade astrocytoma | 28 | 35 |
|  | Grade 3 | 14 | 17 |
|  | Grade 4 | 39 | 48 |
| Recurrence | Absent | 41 | 51 |
|  | Present | 40 | 49 |
| Adjuvant therapy | None | 31 | 38 |
|  | Radiotherapy | 47 | 58 |
|  | Chemoradiotherapy | 3 | 4 |

TABLE 15-continued

The Brain Cancer Patients Characteristics

|  |  | Case number | Percentage (%) |
|---|---|---|---|
| Lethal cell | Negative | 45 | 55.6 |
|  | Positive | 36 | 44.4 |

Abbreviations:
Grade 3, Anaplastic or oligoastrocytoma;
Grade 4, Glioblastoma multiform
†The results of continuous variable are expressed as mean ± SD.

The patients characteristics in this study were similar to the current epidemiologic status, indicating that the results obtained from these cases in an independent cohort study are applicable to brain cancer worldwide. It was therefore decided to use this representative study population to evaluate the role of lethal cell in determining disease status and therapy response of brain cancer patients. Univariate analysis of prognostic significance of lethal cell by the Kaplan-Meier method revealed that the brain cancer patients if associated with a lethal cell tend to have very poor outcome (P<0.001). The 5-year disease-free survival for the patients with a lethal cell was 11.1% versus 41.9% for those patients without lethal cell (P<0.001) and the 5-year overall survival for the patients with a lethal cell was 16.7% versus 59.6% for the negative patients (P<0.001). Cox univariate proportional hazards regression analysis revealed that lethal cell, age, and glioblastoma multiform were significantly associated with higher risk for disease-relapse as well as mortality (P<0.001). Lethal cell in brain cancer patients was further identified as a very powerful prognostic indicator for disease-free survival (HR 3.014, 95% CI 1.777-5.113, P<0.001) as well as for overall survival (HR 4.531, 95% CI 2.463-8.336, P<0.001).

It is interesting to note that of 50 patients subjected to postoperative chemotherapy, lethal cell was also significantly associated with patients' outcome. The brain cancer patients without lethal cell had much better outcome and the patients with a lethal cell predominantly had an evident worse outcome in response to adjuvant chemotherapy and the 5-year survival for the positive patients was 10.0% versus 53.2% for the negative patients (P<0.001). When logistic regression was applied, lethal cell, age and histology were potential prognostic predictors of adjuvant therapy response in univariate analysis. Lethal cell was further identified as the strongest independent prognostic indicator for determining who will benefit from adjuvant therapy of the brain cancer patients (OR 8.081, 95% CI 1.141-57.213, P=0.036).

Lethal cell obviously plays a determinant and instructional role in determining a curable or incurable disease status and all kinds of therapy response of brain cancer patients at all stages. Thus, this invention provides methods and compositions for detection of lethal cell and uses thereof in brain cancer patients. The more aggressive and appropriate treatments definitely are needed to those brain cancer patients associated with a lethal cell. Targeting lethal cell should be as essential and critical as targeting conventional aggressive brain cancer cell in the treatment of brain cancer patients associated with a lethal cell.

Example XII

Figure 4A:
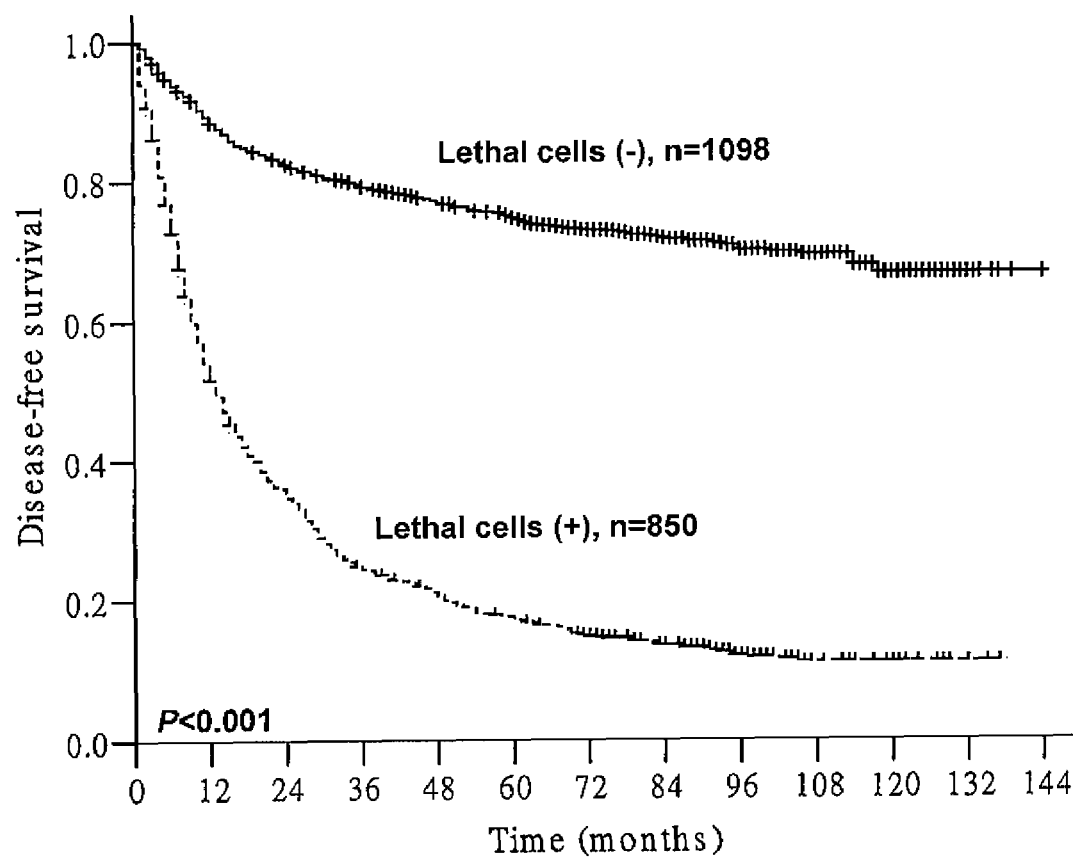
FIG. 4 depicts the disease-free survival (A) and overall survival (B) of various types of cancer patients with respect to lethal cell.
Figure 4B:
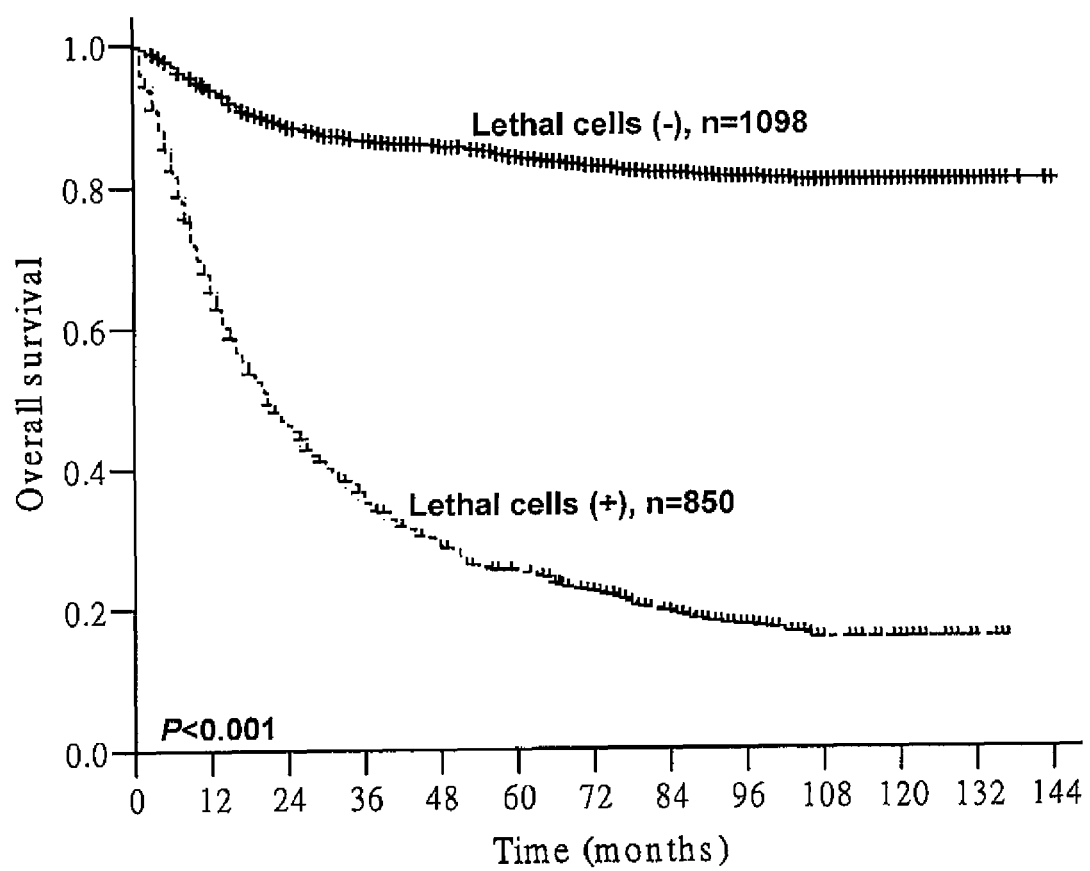

Cancer Patients if Associated with a Lethal Cell Tend to have Very Unfavorable Outcome Even after Aggressive Treatments There were 1948 patients with various types of cancers with complete clinicopathologic data and specimen available for lethal cell study. Of 1948 patients studied (997 male and 951 female) with ages ranging from 1 to 97 years (mean±SD, 56.4±14.8), the types of cancer were bladder cancer in 55 patients, breast cancer in 186 patients, brain cancer in 85 patients, cervical cancer in 161 patients, bile duct cancer in 161 patients, colorectal cancer in 93 patients, endometrial cancer in 30 patients, esophageal cancer in 38 patients, liver cancer in 143 patients, gastric cancer in 152 patients, lung cancer in 169 patients, nasopharyngeal cancer in 92 patients, oral cancer in 134 patients, ovarian cancer in 61 patients, pancreatic cancer in 127 patients, prostate cancer in 83 patients, kidney cancer in 93 patients, and lymphoma in 85 patients. Patients were observed until April, 2006. Approximately 43.6% (850 of 1948) of the cancer patients exhibited a lethal cell (Table 16). The Kaplan-Meier method revealed that the cancer patients if associated with a lethal cell in tumor stroma and/or peripheral blood and/or ascites and/or pleural effusion and/or bone marrow tend to have very poor outcome (P<0.001). The 5-year disease-free survival for the patients with a lethal cell was 17.1% versus 74.7% for those patients without lethal cell (P<0.001, FIG. 4A) and the 5-year overall survival for the patients with a lethal cell was 25.0% versus 84.1% for the patients without lethal cell (P<0.001, FIG. 4B). Most of the cancer patients regardless of the etiological origin of the cancer if associated with a lethal cell tend to develop poor outcome even after aggressive treatments including surgery, chemotherapy, radiotherapy and hormone therapy.

Lethal cell obviously plays a determinant and instructional role in determining a curable or incurable disease status and all kinds of therapy response of various types of cancer patients at all stages. Thus, this invention provides methods and compositions for detection of lethal cell and uses thereof in various types of cancer patients. The more aggressive and appropriate treatments definitely are needed to those cancer patients associated with a lethal cell. Targeting lethal cell should be as essential and critical as targeting conventional aggressive cancer cell in the treatment of cancer patients associated with a lethal cell.

TABLE 16

The Patients Characteristics

|  |  | Case number | Percentage (%) |
|---|---|---|---|
| Cancer type | Bladder cancer | 55 | 2.8 |
|  | Breast cancer | 186 | 9.5 |
|  | Brain cancer | 85 | 4.4 |
|  | Cervical cancer | 161 | 8.3 |
|  | Bile duce cancer | 161 | 8.3 |
|  | Colorectal cancer | 93 | 4.8 |
|  | Endometrial cancer | 30 | 1.5 |
|  | Esophageal cancer | 38 | 1.9 |
|  | Gastric cancer | 152 | 7.8 |
|  | Liver cancer | 143 | 7.3 |
|  | Lung cancer | 169 | 8.7 |
|  | Nasopharyngeal cancer | 92 | 4.7 |
|  | Oral cancer | 134 | 6.9 |
|  | Ovary cancer | 61 | 3.1 |
|  | Pancreatic cancer | 127 | 6.5 |
|  | Prostate cancer | 83 | 4.3 |
|  | Kidney cancer | 93 | 4.8 |
|  | Lymphoma and leukemia | 85 | 4.4 |
| Gender | Male | 997 | 51.2 |
|  | Female | 951 | 48.8 |
| Age | Range (years) | 1-97 | |
|  | Mean ± SD | 56.4 ± 14.8 | |
| Adjuvant therapy | Performed | 680 | 34.9 |
|  | Not performed | 737 | 37.8 |
|  | No record | 533 | 27.3 |

TABLE 16-continued

The Patients Characteristics

|  |  | Case number | Percentage (%) |
|---|---|---|---|
| Status | Alive | 1082 | 55.5 |
|  | Death | 866 | 44.5 |
| Lethal cell | Negative | 1098 | 56.4 |
|  | Positive | 850 | 43.6 |

It is interesting to note that a relatively large population of early-stage cancer patients were found already associated with a lethal cell and failed to have favorable outcome even after potentially curative treatment. Conversely, a relatively large population of advanced-stage cancer patients were found without any lethal cell and had a rather favorable outcome after treatments compared with the same advanced-stage cancer patients with a lethal cell. Thus, the developing pathways and stage of lethal cell and cancer cell are distinctly different.

In conclusions, targeting lethal cell presented in this invention should be as equally essential and critical as targeting the conventional cancer cell in the treatments of various types of cancer patients. More aggressive and appropriate treatments are needed to cure those cancer patients associated with a lethal cell.

What is claimed is:

1. A method for detecting presence of a lethal cell in a subject, which method comprises:
   obtaining a biological sample from the subject;
   determining a bone marrow-derived stem/progenitor cell (BMDSC) in the biological sample; and
   determining the expression profile of PDPK $F_A$/GSK-3α in the bone marrow-derived stem/progenitor cell (BMDSC);
   wherein an aberrant intracellular accumulation of PDPK $F_A$/GSK-3α in the BMDSC indicates the subject has the presence of the lethal cell.

2. The method of claim 1, wherein said expression of PDPK FA/GSK-3α is determined by assessing PDPK FA/GSK-3α protein level.

3. The method of claim 2, wherein PDPK FA/GSK-3α protein expression is determined by immunoassay using antibodies specific for PDPK FA/GSK-3α.

4. The method of claim 1, wherein the aberrant intracellular accumulation of PDPK FA is in both cytoplasmic and nuclear expression level.

5. The method of claim 1, wherein said biological sample is bone marrow, peripheral blood, tissue, tumor, ascites or pleural effusions.

6. The method of claim 1, wherein BMDSC is selected from a group consisting of hematopoietic stem/progenitor cell and mesenchymal stem/progenitor cell.

7. A method for monitoring disease status and therapy response of cancer patients, which method comprises:
   obtaining a biological sample from the cancer patients;
   determining a bone marrow-derived stem/progenitor cell (BMDSC) in the biological sample; and determining the expression profile of PDPK $F_A$/GSK-3α in the bone marrow-derived stem/progenitor cell (BMDSC);
   wherein an aberrant intracellular accumulation of PDPK $F_A$/GSK-3α in BMDSC predicts disease status and therapy response of cancer patients.

8. The method of claim 7, wherein therapy response is selected from the group consisting of surgery, chemotherapy, radiotherapy and hormone therapy.

9. The method of claim 7, wherein the cancer patient is selected from the group consisting of bladder, breast, brain, bile duct, cervical, colorectal, endometrial, esophageal, gastric, liver, lung, nasopharyngeal, oral, ovarian, pancreatic, prostate and kidney cancers, leukemia and lymphoma.

10. A kit for detection of lethal cell in a biological sample, comprising
   instructions to obtain a biologic sample from a subject;
   instructions to determine a bone marrow-derived stem/progenitor cell (BMDSC) in the biological sample;
   instructions to determine the expression profile of PDPK FA/GSK-3α in said bone marrow-derived stem/progenitor cell (BMDSC),
   specific antibody and reagents to assessing PDPK FA/GSK-3α protein expressions pattern for determining the presence of a lethal cell.

* * * * *